US009814600B2

(12) United States Patent
Shulock et al.

(10) Patent No.: US 9,814,600 B2
(45) Date of Patent: Nov. 14, 2017

(54) SELECTIVELY EXPANDING SPINE CAGE WITH ENHANCED BONE GRAFT INFUSION

(71) Applicant: Howmedica Osteonics Corp., Mahwah, NJ (US)

(72) Inventors: Damien J. Shulock, San Francisco, CA (US); John E. Ashley, Danville, CA (US); Thomas Grotz, Novato, CA (US); Rudy Pretti, Auburn, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 0 days.

(21) Appl. No.: 14/689,634

(22) Filed: Apr. 17, 2015

(65) Prior Publication Data

US 2015/0216676 A1   Aug. 6, 2015

Related U.S. Application Data

(63) Continuation of application No. 13/799,047, filed on Mar. 13, 2013, now Pat. No. 9,028,550, which is a
(Continued)

(51) Int. Cl.
*A61F 2/44* (2006.01)
*A61F 2/46* (2006.01)
(Continued)

(52) U.S. Cl.
CPC ............ *A61F 2/4465* (2013.01); *A61F 2/441* (2013.01); *A61F 2/442* (2013.01); *A61F 2/4601* (2013.01);
(Continued)

(58) Field of Classification Search
CPC ............ A61B 17/8822; A61B 17/7097; A61B 17/8805; A61B 17/1671; A61B 17/8816;
(Continued)

(56) References Cited

U.S. PATENT DOCUMENTS 3,875,595 A   4/1975 Froning
4,932,975 A   6/1990 Main et al.
(Continued)

FOREIGN PATENT DOCUMENTS

EP   1415624 A1   5/2004
EP   1442715 A2   8/2004
(Continued)

OTHER PUBLICATIONS

International Search Report and Written Opinion dated Sep. 22, 2011 in related International Application No. PCT/US2011/037929.
(Continued)

*Primary Examiner* — Eduardo C Robert
*Assistant Examiner* — Tara R Carter
(74) *Attorney, Agent, or Firm* — Lerner, David, Littenberg, Krumholz & Mentlik, LLP

(57) ABSTRACT

A selectively expanding spine cage has a minimized cross section in its unexpanded state that is smaller than the diameter of the neuroforamen through which it passes in the distracted spine. The cage conformably engages between the endplates of the adjacent vertebrae to effectively distract the anterior disc space, stabilize the motion segments and eliminate pathologic spine motion. Expanding selectively (anteriorly, along the vertical axis of the spine) rather than uniformly, the cage height increases and holds the vertebrae with fixation forces greater than adjacent bone and soft tissue failure forces in natural lordosis. Stability is thus achieved immediately, enabling patient function by eliminating painful motion. The cage shape intends to rest proximate to the anterior column cortices securing the desired spread and fixation, allowing for bone graft in, around, and through the implant for arthrodesis whereas for arthroplasty it fixes to endpoints but cushions the spine naturally.

22 Claims, 15 Drawing Sheets

Related U.S. Application Data continuation-in-part of application No. 13/183,080, filed on Jul. 14, 2011, now Pat. No. 8,454,695, which is a continuation of application No. 11/535,432, filed on Sep. 26, 2006, now Pat. No. 7,985,256.

(60) Provisional application No. 60/720,784, filed on Sep. 26, 2005.

(51) Int. Cl.
    *A61F 2/30*     (2006.01)
    *A61F 2/28*     (2006.01)
    *A61F 2/48*     (2006.01)

(52) U.S. Cl.
CPC ......... *A61F 2/4611* (2013.01); *A61F 2/30771* (2013.01); *A61F 2002/2835* (2013.01); *A61F 2002/3055* (2013.01); *A61F 2002/30062* (2013.01); *A61F 2002/30133* (2013.01); *A61F 2002/30235* (2013.01); *A61F 2002/30433* (2013.01); *A61F 2002/30538* (2013.01); *A61F 2002/30563* (2013.01); *A61F 2002/30579* (2013.01); *A61F 2002/30581* (2013.01); *A61F 2002/30583* (2013.01); *A61F 2002/30591* (2013.01); *A61F 2002/30593* (2013.01); *A61F 2002/30596* (2013.01); *A61F 2002/30598* (2013.01); *A61F 2002/30604* (2013.01); *A61F 2002/30617* (2013.01); *A61F 2002/30622* (2013.01); *A61F 2002/30772* (2013.01); *A61F 2002/30777* (2013.01); *A61F 2002/4475* (2013.01); *A61F 2002/4627* (2013.01); *A61F 2002/4629* (2013.01); *A61F 2002/4631* (2013.01); *A61F 2002/4666* (2013.01); *A61F 2002/485* (2013.01); *A61F 2210/0085* (2013.01); *A61F 2220/0041* (2013.01); *A61F 2230/0015* (2013.01); *A61F 2230/0069* (2013.01); *A61F 2250/0006* (2013.01); *A61F 2250/0097* (2013.01); *A61F 2310/00017* (2013.01); *A61F 2310/00023* (2013.01); *A61F 2310/00796* (2013.01)

(58) Field of Classification Search
CPC ........ A61B 17/8802; A61B 2017/0256; A61B 17/68; A61B 17/7275; A61B 17/70; A61B 17/8852; A61B 17/025; A61B 17/00539
USPC .............. 606/246–249, 90, 92–94; 623/17.11–17.16
See application file for complete search history.

(56) References Cited

U.S. PATENT DOCUMENTS

| | | | |
|---|---|---|---|
| 4,969,888 A | 11/1990 | Scholten et al. | |
| 5,236,460 A * | 8/1993 | Barber | 623/17.15 |
| 5,653,763 A | 8/1997 | Errico et al. | |
| 5,665,122 A | 9/1997 | Kambin | |
| 5,723,013 A | 3/1998 | Jeanson et al. | |
| 5,827,328 A | 10/1998 | Buttermann | |
| 5,865,848 A | 2/1999 | Baker | |
| 5,916,267 A * | 6/1999 | Tienboon | 623/17.11 |
| 5,980,522 A | 11/1999 | Koros et al. | |
| 5,989,290 A | 11/1999 | Biedermann et al. | |
| 6,039,761 A | 3/2000 | Li et al. | |
| 6,102,950 A | 8/2000 | Vaccaro | |
| 6,127,597 A | 10/2000 | Beyar et al. | |
| 6,176,881 B1 | 1/2001 | Schar et al. | |
| 6,193,756 B1 | 2/2001 | Studer et al. | |
| 6,214,012 B1 * | 4/2001 | Karpman et al. | 606/93 |
| 6,296,665 B1 | 10/2001 | Strnad et al. | |
| 6,371,989 B1 | 4/2002 | Chauvin et al. | |
| 6,375,682 B1 | 4/2002 | Fleischmann et al. | |
| 6,375,683 B1 | 4/2002 | Crozet et al. | |
| 6,395,032 B1 | 5/2002 | Gauchet | |
| 6,454,806 B1 | 9/2002 | Cohen et al. | |
| 6,562,074 B2 * | 5/2003 | Gerbec | A61F 2/4455 623/17.15 |
| 6,582,467 B1 | 6/2003 | Teitelbaum et al. | |
| 6,585,699 B2 | 7/2003 | Ljunggreen et al. | |
| 6,692,495 B1 | 2/2004 | Zacouto | |
| 6,719,796 B2 | 4/2004 | Cohen et al. | |
| 6,723,126 B1 | 4/2004 | Berry | |
| 6,730,088 B2 | 5/2004 | Yeh | |
| 6,764,491 B2 | 7/2004 | Frey et al. | |
| 6,830,570 B1 | 12/2004 | Frey et al. | |
| 6,835,207 B2 | 12/2004 | Zacouto et al. | |
| 6,866,682 B1 | 3/2005 | An et al. | |
| 6,875,235 B2 | 4/2005 | Ferree | |
| 6,953,477 B2 | 10/2005 | Berry | |
| 6,960,232 B2 | 11/2005 | Lyons et al. | |
| 6,981,989 B1 | 1/2006 | Fleischmann et al. | |
| 7,001,431 B2 | 2/2006 | Bao et al. | |
| 7,018,415 B1 | 3/2006 | McKay | |
| 7,018,416 B2 | 3/2006 | Hanson et al. | |
| 7,060,037 B2 | 6/2006 | Lussier et al. | |
| 7,060,073 B2 | 6/2006 | Frey et al. | |
| 7,066,958 B2 | 6/2006 | Ferree | |
| 7,094,257 B2 | 8/2006 | Mujwid et al. | |
| 7,166,110 B2 | 1/2007 | Yundt | |
| 7,204,853 B2 | 4/2007 | Gordon et al. | |
| 7,214,243 B2 | 5/2007 | Taylor | |
| 7,217,293 B2 | 5/2007 | Branch, Jr. | |
| 7,282,063 B2 | 10/2007 | Cohen et al. | |
| 7,291,150 B2 | 11/2007 | Graf | |
| 7,291,158 B2 | 11/2007 | Crow et al. | |
| 7,316,686 B2 | 1/2008 | Dorchak et al. | |
| 7,316,714 B2 | 1/2008 | Gordon et al. | |
| 7,351,261 B2 | 4/2008 | Casey | |
| 7,407,513 B2 | 8/2008 | Alleyne et al. | |
| 7,419,505 B2 | 9/2008 | Fleischmann et al. | |
| 7,452,359 B1 | 11/2008 | Michelson | |
| 7,470,273 B2 | 12/2008 | Dougherty-Shah | |
| 7,481,812 B2 | 1/2009 | Frey et al. | |
| 7,485,145 B2 | 2/2009 | Purcell | |
| 7,507,241 B2 | 3/2009 | Levy et al. | |
| 7,520,900 B2 | 4/2009 | Trieu | |
| 7,563,284 B2 | 7/2009 | Coppes et al. | |
| 7,563,286 B2 | 7/2009 | Gerber et al. | |
| 7,621,956 B2 | 11/2009 | Paul et al. | |
| 7,628,815 B2 | 12/2009 | Baumgartner et al. | |
| 7,670,359 B2 | 3/2010 | Yundt | |
| 7,708,779 B2 | 5/2010 | Edie et al. | |
| 7,722,674 B1 | 5/2010 | Grotz | |
| 7,731,752 B2 | 6/2010 | Edie et al. | |
| 7,731,753 B2 | 6/2010 | Reo et al. | |
| 7,771,480 B2 | 8/2010 | Navarro et al. | |
| 7,794,501 B2 | 9/2010 | Edie et al. | |
| 7,806,935 B2 | 10/2010 | Navarro et al. | |
| 7,819,921 B2 | 10/2010 | Grotz | |
| 7,824,444 B2 | 11/2010 | Biscup et al. | |
| 7,824,445 B2 | 11/2010 | Biro et al. | |
| 7,854,766 B2 | 12/2010 | Moskowitz et al. | |
| 7,862,618 B2 | 1/2011 | White et al. | |
| 7,883,543 B2 * | 2/2011 | Sweeney | 623/17.15 |
| 7,935,124 B2 | 5/2011 | Frey et al. | |
| 7,967,863 B2 | 6/2011 | Frey et al. | |
| 7,967,867 B2 | 6/2011 | Barreiro et al. | |
| 7,985,231 B2 | 7/2011 | Sankaran | |
| 7,985,256 B2 | 7/2011 | Grotz et al. | |
| 8,021,395 B2 | 9/2011 | Ben-Mokhtar et al. | |
| 8,025,680 B2 | 9/2011 | Hayes et al. | |
| 8,057,549 B2 | 11/2011 | Butterman et al. | |
| 8,062,368 B2 | 11/2011 | Heinz et al. | |
| 8,062,373 B2 | 11/2011 | Fabian, Jr. | |
| 8,070,813 B2 | 12/2011 | Grotz et al. | |
| 8,105,382 B2 | 1/2012 | Olmos et al. | |
| 8,153,785 B2 | 4/2012 | Khire et al. | |
| 8,187,331 B2 | 5/2012 | Strohkirch, Jr. et al. | |
| 8,192,495 B2 | 6/2012 | Simpson et al. | |
| 8,267,939 B2 | 9/2012 | Cipoletti et al. | |

(56) References Cited

U.S. PATENT DOCUMENTS

| | | | |
|---|---|---|---|
| 8,273,124 B2 | 9/2012 | Renganath et al. | |
| 8,353,961 B2 | 1/2013 | McClintock et al. | |
| 8,366,777 B2 | 2/2013 | Matthis et al. | |
| 8,394,143 B2 | 3/2013 | Grotz et al. | |
| 8,435,296 B2 | 5/2013 | Kadaba et al. | |
| 8,454,695 B2 | 6/2013 | Grotz et al. | |
| 8,696,751 B2 | 4/2014 | Ashley et al. | |
| 2001/0056302 A1* | 12/2001 | Boyer et al. | 623/17.15 |
| 2002/0128716 A1 | 9/2002 | Cohen et al. | |
| 2002/0136146 A1 | 9/2002 | Lee et al. | |
| 2002/0138146 A1 | 9/2002 | Jackson | |
| 2002/0151976 A1 | 10/2002 | Foley et al. | |
| 2003/0114899 A1 | 6/2003 | Woods et al. | |
| 2003/0130739 A1* | 7/2003 | Gerbec | A61F 2/4455 623/17.15 |
| 2004/0030346 A1 | 2/2004 | Frey et al. | |
| 2004/0088054 A1 | 5/2004 | Berry | |
| 2004/0097928 A1 | 5/2004 | Zdeblick et al. | |
| 2004/0133273 A1 | 7/2004 | Cox | |
| 2004/0181229 A1* | 9/2004 | Michelson | 606/69 |
| 2004/0186576 A1 | 9/2004 | Biscup et al. | |
| 2005/0033437 A1 | 2/2005 | Bao et al. | |
| 2005/0043800 A1 | 2/2005 | Paul et al. | |
| 2005/0049590 A1 | 3/2005 | Alleyne et al. | |
| 2005/0085910 A1 | 4/2005 | Sweeney | |
| 2005/0107881 A1 | 5/2005 | Alleyne et al. | |
| 2005/0113842 A1 | 5/2005 | Bertagnoli et al. | |
| 2005/0197702 A1 | 9/2005 | Coppes et al. | |
| 2005/0216084 A1 | 9/2005 | Fleischmann et al. | |
| 2005/0229433 A1 | 10/2005 | Cachia | |
| 2005/0251260 A1 | 11/2005 | Gerber et al. | |
| 2005/0273169 A1 | 12/2005 | Purcell | |
| 2005/0273170 A1 | 12/2005 | Navarro et al. | |
| 2005/0273171 A1 | 12/2005 | Gordon et al. | |
| 2006/0036259 A1 | 2/2006 | Carl et al. | |
| 2006/0085073 A1 | 4/2006 | Raiszadeh | |
| 2006/0089719 A1 | 4/2006 | Trieu | |
| 2006/0106416 A1 | 5/2006 | Raymond et al. | |
| 2006/0116767 A1 | 6/2006 | Magerl et al. | |
| 2006/0142860 A1 | 6/2006 | Navarro et al. | |
| 2006/0149377 A1 | 7/2006 | Navarro et al. | |
| 2006/0167547 A1 | 7/2006 | Suddaby | |
| 2006/0200244 A1 | 9/2006 | Assaker | |
| 2006/0235426 A1 | 10/2006 | Lim et al. | |
| 2006/0235535 A1 | 10/2006 | Ferree et al. | |
| 2006/0264968 A1 | 11/2006 | Frey et al. | |
| 2007/0050030 A1 | 3/2007 | Kim | |
| 2007/0050033 A1 | 3/2007 | Reo et al. | |
| 2007/0073395 A1 | 3/2007 | Baumgartner et al. | |
| 2007/0093901 A1 | 4/2007 | Grotz et al. | |
| 2007/0093903 A1 | 4/2007 | Cheng | |
| 2007/0123987 A1 | 5/2007 | Bernstein | |
| 2007/0179611 A1 | 8/2007 | DiPoto et al. | |
| 2007/0233254 A1 | 10/2007 | Grotz et al. | |
| 2007/0255409 A1 | 11/2007 | Dickson et al. | |
| 2007/0255413 A1 | 11/2007 | Edie et al. | |
| 2007/0255415 A1 | 11/2007 | Edie et al. | |
| 2007/0270961 A1 | 11/2007 | Ferguson | |
| 2007/0270964 A1 | 11/2007 | Strohkirch et al. | |
| 2007/0288092 A1 | 12/2007 | Bambakidis | |
| 2008/0021555 A1 | 1/2008 | White et al. | |
| 2008/0021556 A1 | 1/2008 | Edie | |
| 2008/0058930 A1 | 3/2008 | Edie et al. | |
| 2008/0058931 A1 | 3/2008 | White et al. | |
| 2008/0065082 A1 | 3/2008 | Chang et al. | |
| 2008/0065220 A1 | 3/2008 | Alleyne et al. | |
| 2008/0065221 A1 | 3/2008 | Alleyne et al. | |
| 2008/0077150 A1 | 3/2008 | Nguyen | |
| 2008/0086276 A1 | 4/2008 | Naka et al. | |
| 2008/0097441 A1 | 4/2008 | Hayes et al. | |
| 2008/0103601 A1 | 5/2008 | Biro et al. | |
| 2008/0114467 A1 | 5/2008 | Capote et al. | |
| 2008/0140207 A1 | 6/2008 | Olmos et al. | |
| 2008/0147193 A1 | 6/2008 | Matthis et al. | |
| 2008/0147194 A1 | 6/2008 | Grotz et al. | |
| 2008/0161933 A1 | 7/2008 | Grotz et al. | |
| 2008/0177387 A1 | 7/2008 | Parimore et al. | |
| 2008/0215153 A1 | 9/2008 | Butterman et al. | |
| 2008/0281424 A1 | 11/2008 | Parry et al. | |
| 2008/0288073 A1 | 11/2008 | Renganath et al. | |
| 2008/0300598 A1 | 12/2008 | Barreiro et al. | |
| 2009/0005819 A1 | 1/2009 | Ben-Mokhtar et al. | |
| 2009/0005874 A1 | 1/2009 | Fleischmann et al. | |
| 2009/0018661 A1 | 1/2009 | Kim et al. | |
| 2009/0043312 A1 | 2/2009 | Koulisis et al. | |
| 2009/0048676 A1 | 2/2009 | Fabian, Jr. | |
| 2009/0105836 A1 | 4/2009 | Frey et al. | |
| 2009/0171389 A1 | 7/2009 | Sankaran | |
| 2009/0204215 A1 | 8/2009 | McClintock et al. | |
| 2009/0216331 A1 | 8/2009 | Grotz et al. | |
| 2009/0222100 A1 | 9/2009 | Cipoletti et al. | |
| 2009/0270987 A1 | 10/2009 | Heinz et al. | |
| 2010/0057204 A1 | 3/2010 | Kadaba et al. | |
| 2010/0145455 A1 | 6/2010 | Simpson et al. | |
| 2010/0145456 A1 | 6/2010 | Simpson et al. | |
| 2011/0130835 A1 | 6/2011 | Ashley et al. | |
| 2011/0270398 A1 | 11/2011 | Grotz et al. | |
| 2011/0288646 A1 | 11/2011 | Moskowitz et al. | |
| 2012/0116518 A1 | 5/2012 | Grotz et al. | |
| 2012/0245695 A1 | 9/2012 | Simpson et al. | |

FOREIGN PATENT DOCUMENTS

| | | |
|---|---|---|
| WO | 03003951 A1 | 1/2003 |
| WO | 2004016205 A2 | 2/2004 |
| WO | 2004016250 A1 | 2/2004 |
| WO | 2006044786 A2 | 4/2006 |
| WO | 2007124078 A2 | 11/2007 |
| WO | 2008011371 A2 | 1/2008 |
| WO | 2008039811 A2 | 4/2008 |
| WO | 2008086276 A2 | 7/2008 |
| WO | 2008112607 A2 | 9/2008 |
| WO | 2008121251 A2 | 10/2008 |
| WO | 2008148210 A1 | 12/2008 |
| WO | 2009033100 A1 | 3/2009 |
| WO | 2009105182 A1 | 8/2009 |
| WO | 2010068725 A2 | 6/2010 |
| WO | 2010074704 A1 | 7/2010 |
| WO | 2011150077 A1 | 12/2011 |

OTHER PUBLICATIONS

International Search Report and Written Opinion dated Nov. 11, 2010, in International Application No. PCT/US2010/031247 entitled "Insertion Handle for Implant."

International Search Report and Written Opinion dated May 6, 2009 in related International Application No. PCT/US2009/000974 filed Feb. 17, 2009.

International Search Report and Written Opinion dated Aug. 13, 2010, in related International Application No. PCT/US2009/067446 filed Dec. 10, 2009.

International Search Report and Written Opinion dated Jun. 30, 2009, in related International Application No. PCT/US2008/003776 filed Mar. 21, 2008.

International Search Report and Written Opinion dated Apr. 10, 2008 in related International Application No. PCT/US2007/079474.

International Search Report and Written Opinion dated Nov. 11, 2010 in International Application No. PCT/US2010/031247 entitled "Insertion Handle for Implant."

International Search Report and Written Opinion dated Jun. 5, 2009 for related PCT/US2009/000974.

International Search Report and Written Opinion dated May 6, 2009, in related International Application No. PCT/US2009/000974 filed Feb. 17, 2009.

International Search Report and Written Opinion dated Apr. 10, 2008, in related International Application No. PCT/US2007/079474.

International Search Report for PCT/US2007/079474 dated Apr. 10, 2008.

Written Opinion of the International Searching Authority for PCT/US2007/079474 dated Apr. 10, 2008.

(56) References Cited

OTHER PUBLICATIONS

Extended European Search Report for Application No. 14159365.7 dated Jun. 18, 2014.

* cited by examiner

SELECTIVELY EXPANDING SPINE CAGE WITH ENHANCED BONE GRAFT INFUSION

CROSS REFERENCE TO RELATED APPLICATIONS

This application is a continuation of U.S. patent application Ser. No. 13/799,047, filed Mar. 13, 2013, now pending, which in turn, is a continuation-in-part of U.S. patent application Ser. No. 13/183,080 filed Jul. 14, 2011, which is a continuation of U.S. patent application Ser. No. 11/535,432 filed Sep. 26, 2006, which claims priority from U.S. Provisional Application 60/720,784 filed Sep. 26, 2005, the disclosures of which are herein incorporated by reference.

FIELD OF THE INVENTION

The present invention generally relates to medical devices for stabilizing the vertebral motion segment. More particularly, the field of the invention relates to a remotely activated, hydraulically controllable, selectively expanding cage (SEC) and method of insertion for providing controlled spinal correction in three dimensions for improved spinal intervertebral body distraction and fusion.

BACKGROUND

Conventional spine cages or implants are typically characterized by a kidney bean-shaped body comprising a hydroxyapatite-coated surface provided on the exterior surface for contact with adjacent vertebral segments or endplates which are shown in FIG. 1. A conventional spine cage is typically inserted in tandem posteriorly through the neuroforamen of the distracted spine after a trial implant creates a pathway.

Such existing devices for interbody stabilization have important and significant limitations. These limitations include an inability to expand and distract the endplates. Current devices for interbody stabilization include static spacers composed of titanium, PEEK, and high performance thermoplastic polymer produced by VICTREX, (Victrex USA Inc, 3A Caledon Court, Greenville, S.C. 29615), carbon fiber, or resorbable polymers. Current interbody spacers do not maintain interbody lordosis and can contribute to the formation of a straight or even kyphotic segment and the clinical problem of "flatback syndrome." Separation of the endplates increases space available for the neural elements, specifically the neural foramen. Existing static cages do not reliably improve space for the neural elements. Therefore, what is needed is an expanding cage that will increase space for the neural elements posteriorly between the vertebral bodies, or at least maintain the natural bone contours to avoid neuropraxia (nerve stretch) or encroachment.

Another problem with conventional devices of interbody stabilization includes poor interface between bone and biomaterial. Conventional static interbody spacers form a weak interface between bone and biomaterial. Although the surface of such implants is typically provided with a series of ridges or coated with hydroxyapetite, the ridges may be in parallel with applied horizontal vectors or side-to-side motion. That is, the ridges or coatings offer little resistance to movement applied to either side of the endplates. Thus, nonunion is common in allograft, titanium and polymer spacers, due to motion between the implant and host bone. Conventional devices typically do not expand between adjacent vertebrae.

Therefore, what is needed is a way to expand an implant to develop immediate fixation forces that can exceed the ultimate strength at healing. Such an expandable implant ideally will maximize stability of the interface and enhance stable fixation. The immediate fixation of such an expandable interbody implant advantageously will provide stability that is similar to that achieved at the time of healing. Such an implant would have valuable implications in enhancing early post-operative rehabilitation for the patient.

Another problem of conventional interbody spacers is their large diameter requiring wide exposure. Existing devices used for interbody spacers include structural allograft, threaded cages, cylindrical cages, and boomerang-shaped cages. Conventional devices have significant limitation with regard to safety and efficacy. Regarding safety of the interbody spacers, injury to neural elements may occur with placement from an anterior or posterior approach. A conventional spine cage lacks the ability to expand, diminishing its fixation capabilities.

The risks to neural elements are primarily due to the disparity between the large size of the cage required to adequately support the interbody space, and the small space available for insertion of the device, especially when placed from a posterior or transforaminal approach. Existing boomerang cages are shaped like a partially flattened kidney bean. Their implantation requires a wide exposure and potential compromise of vascular and neural structures, both because of their inability to enter small and become larger, and due to the fact that their insertion requires mechanical manipulation during insertion and expanding of the implant. Once current boomerang implants are prepared for insertion via a trial spacer to make a pathway toward the anterior spinal column, the existing static cage is shoved toward the end point with the hope that it will reach a desired anatomic destination. Given the proximity of nerve roots and vascular structures to the insertion site, and the solid, relatively large size of conventional devices, such constraints predispose a patient to foraminal (nerve passage site) encroachment, and possible neural and vascular injury.

Therefore, what is needed is a minimally invasive expanding spine cage that is capable of insertion with minimal invasion into a smaller aperture. Such a minimally invasive spine cage advantageously could be expanded with completely positional control or adjustment in three dimensions by hydraulic force application through a connected thin, pliable hydraulic line. The thin hydraulic line would take the place of rigid insertional tools, thereby completely preventing trauma to delicate nerve endings and nerve roots about the spinal column. Due to the significant mechanical leverage developed by a hydraulic control system, the same expanding cage could advantageously be inserted by a minimally-sized insertion guiding rod tool capable of directing the cage through the transforaminal approach to a predetermined destination, also with reduced risk of trauma to nerve roots. That is, the mechanical advantage is provided by a hydraulic control system controlled by the physician external to the patient.

The minimally-sized insertion tool could house multiple hydraulic lines for precise insertion and expansion of the cage, and simply detached from the expanded cage after insertion. It is noted that in such a hydraulic system, a smaller, thinner line advantageously also increases the pounds per inch of adjusting force necessary to achieve proper expansion of the implant (as opposed to a manually powered or manipulated surgical tool) that must apply force directly at the intervention site. That is, for a true minimally-invasive approach to spinal implant surgery what is needed is an apparatus and method for providing the significant amount of force necessary to properly expand and adjust the cage against the vertebral endplates, safely away from the intervention site.

What is also needed is a smaller expanding spine cage that is easier to operatively insert into a patient with minimal surgical trauma in contrast to conventional, relatively large devices that create the needless trauma to nerve roots in the confined space of the vertebral region.

Existing interbody implants have limited space available for bone graft. Adequate bone graft or bone graft substitute is critical for a solid interbody arthrodesis. It would be desirable to provide an expandable interbody cage that will permit a large volume of bone graft material to be placed within the cage and around it, to fill the intervertebral space. Additionally, conventional interbody implants lack the ability to stabilize endplates completely and prevent them from moving. Therefore, what is also needed is an expanding spine cage wherein the vertebral end plates are subject to forces that both distract them apart, and hold them from moving. Such an interbody cage would be capable of stabilization of the motion segment, thereby reducing micromotion, and discouraging the pseudoarthrosis (incomplete fusion) and pain.

Ideally, what is needed is a spine cage or implant that is capable of increasing its expansion in width anteriorly to open like a clam, spreading to a calculated degree. Furthermore, what is needed is a spine cage that can adjust the amount of not only overall anterior expansion, but also medial and lateral variable expansion so that both the normal lordotic curve is maintained, and adjustments can be made for scoliosis or bone defects. Such a spine cage or implant would permit restoration of normal spinal alignment after surgery and hold the spine segments together rigidly, mechanically, until healing occurs.

What is also needed is an expanding cage or implant that is capable of holding the vertebral or joint sections with increased pullout strength to minimize the chance of implant fixation loss during the period when the implant is becoming incorporated into the arthrodesis bone block.

It would also be desirable if such a cage could expand anteriorly away from the neural structures and along the axis of the anterior spinal column, rather than uniformly which would take up more space inside the vertebral body surfaces.

SUMMARY OF THE DISCLOSURE

In one implementation, the present disclosure is directed to a selectively expandable spinal implant for insertion between vertebrae of a patient. The selectively expandable spinal implant comprises a cylinder block defining at least first and second cylinders and comprising a base configured for resting on a first vertebrae; at least first and second pistons respectively received in the at least first and second cylinders, the pistons being extendable to impart a desired spinal correction; and a bone engaging plate attached to the pistons opposite the base for engaging a second vertebrae in response to extension of the pistons.

In another implementation, the present disclosure is directed to an apparatus for providing spinal correction. The apparatus includes an implant body configured and dimensioned for placement in an intervertebral space, the body defining a central cavity extending through the body configured to receive bone graft material and communicate with the intervertebral space for infusion of the graft material into the intervertebral space when placed therein, and a bone graft supply passage extending through the body and communicating with the central cavity; a bone graft material supply port disposed on the implant body in communication with the bone graft supply passage, the port configured for attachment of a bone graft material supply line; first and second extendable members mounted on the body, one each disposed on an opposite side of the central cavity, the members extendable from a first unexpanded height and to at least one expanded height; and a plate with a bone engaging surface mounted on the first and second extendable members, the plate defining an opening aligned with the central cavity for passage there through of bone graft material from the central cavity.

In yet another implementation, the present disclosure is directed to an apparatus for providing spinal correction. The apparatus includes an implant body configured and dimensioned for placement in an intervertebral space with a surface configured as a bone engaging surface, the body configured as a cylinder block defining first and second cylinders opening opposite the bone engaging surface and communicating with at least one hydraulic fluid passage, a central, bone graft material receiving cavity extending through the body, and a bone graft supply passage communicating with the central cavity, wherein the central cavity is configured to open to intervertebral space for infusion of the graft material into the intervertebral space when placed therein; first and second extendable pistons sealingly received in the cylinders; a top plate with an opposed bone engaging surface mounted on the first and second pistons, the top plate extendable with the pistons from a first unexpanded implant height and to at least one expanded implant height, the top plate defining an opening aligned with the central cavity for passage there through of bone graft material from the central cavity; a bone graft material supply port disposed on the implant body in communication with the bone graft supply passage, the port configured for attachment of a bone graft material supply line; a hydraulic supply port disposed on the implant body adjacent the bone graft material supply port, the hydraulic supply port communicating with the at least one hydraulic fluid passage; and an attachment port disposed on the implant body adjacent the supply port, the attachment port being configured to receive and secure an implant insertion tool.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
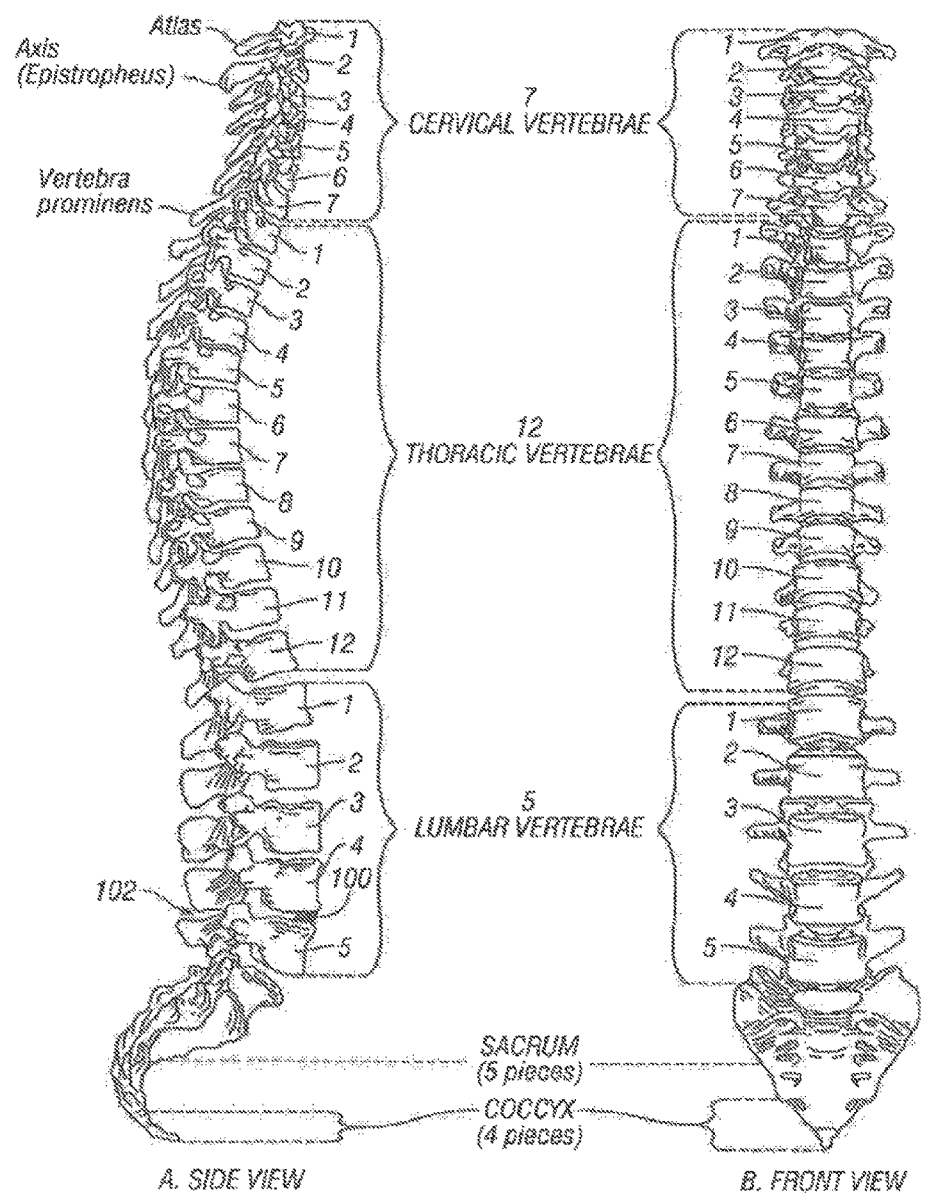
FIG. 1 is a representation of the vertebral column showing posterior insertion and placement of the SEC between the number 4 and 5 lumbar vertebrae according to an aspect of the invention. Whereas this diagram shows the implant anteriorly in the vertebral interspace between lumbar bones 4 and 5, the majority of lumbar fusions are performed between L5 and S1, into which implants are secured. The SEC can be used at any spinal level the surgeon deems in need of fusion.

Referring to FIG. 1, vertebral segments or end plates are shown with an average 8 mm gap representing an average intervertebral space. A complete discectomy is performed prior to the insertion of the SEC 100. The intervertebral disc occupying space 102 is removed using standard techniques including rongeur, curettage, and endplate preparation to bleeding subcondral bone. The posterior longitudinal ligament is divided to permit expansion of the intervertebral space.

The intervertebral space 102 is distracted to about 10 mm using a rotating spatula (Not shown. This is a well-known device that looks like a wide screw driver that can be placed into the disc space horizontally and turned 90 degrees to separate the endplates).

Figure 2:
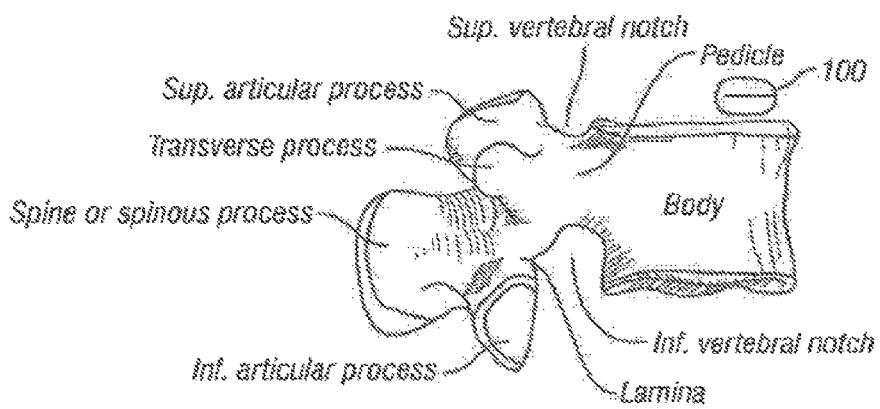
FIG. 2 is a side view of a vertebral body showing the placement of the SEC according to an aspect of the invention.
Figure 3:
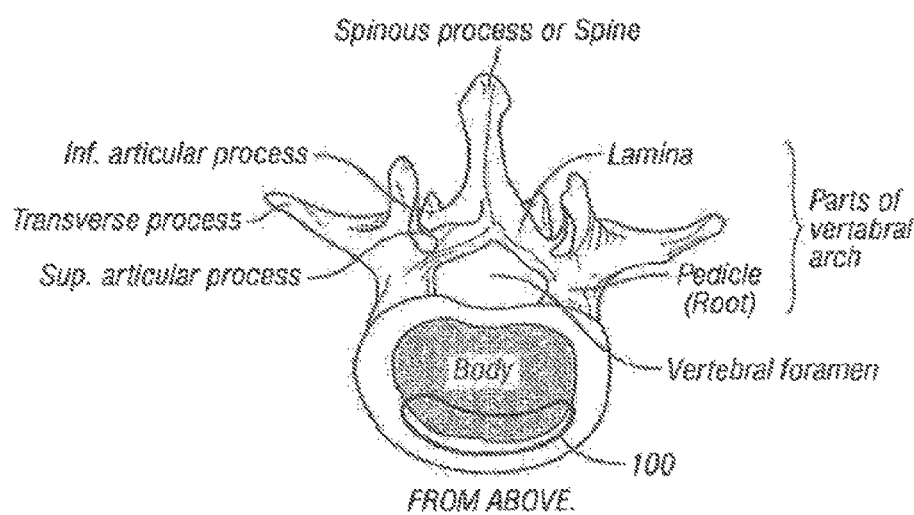
FIG. 3 is a top view of a vertebral body showing placement of the SEC according to an aspect of the invention.

The SEC is inserted posteriorly (in the direction of arrow 102 between the no. 4 and 5 lumbar vertebrae as shown in FIG. 1 (lateral view) or into any selected intervertebral space. In accordance with an aspect of the invention, the SEC is reduced to small size in its unexpanded state to enable it to be inserted posteriorly through space 102 as shown in FIG. 1. In one exemplary embodiment, dimensions of an SEC are: 12 mm wide, 10 mm high and 28 mm long to facilitate posterior insertion and thereby minimize trauma to the patient and risk of injury to nerve roots. Once in place this exemplary SEC can expand to 16 mm, or 160 percent of its unexpanded size, enabling 20 degrees or more of spinal correction medial and lateral. FIGS. 2 and 3 are a side view and top view, respectively, showing the placement of the SEC 100 on a vertebral body.

Figure 4A:
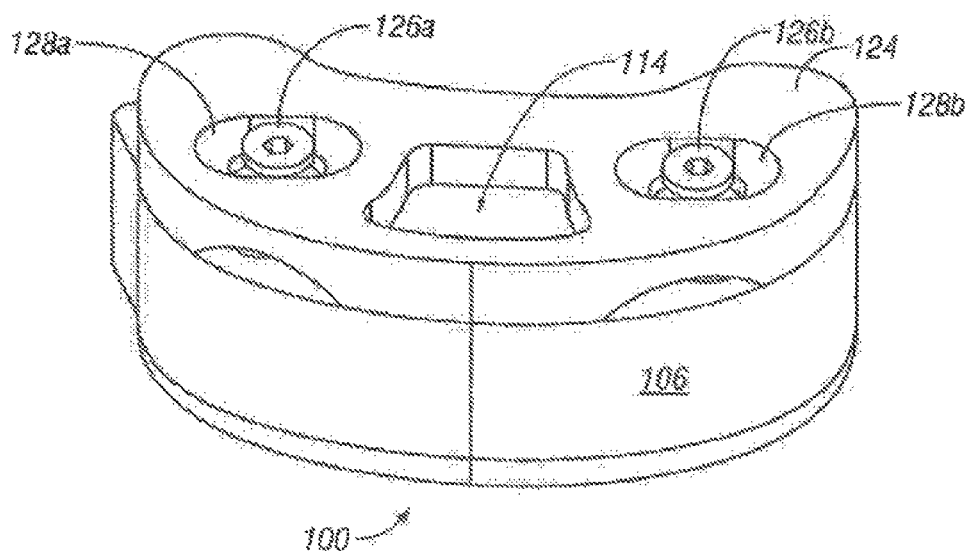
FIG. 4A is a front perspective view of the SEC in an unexpanded state according to an aspect of the invention.
Figure 4B:
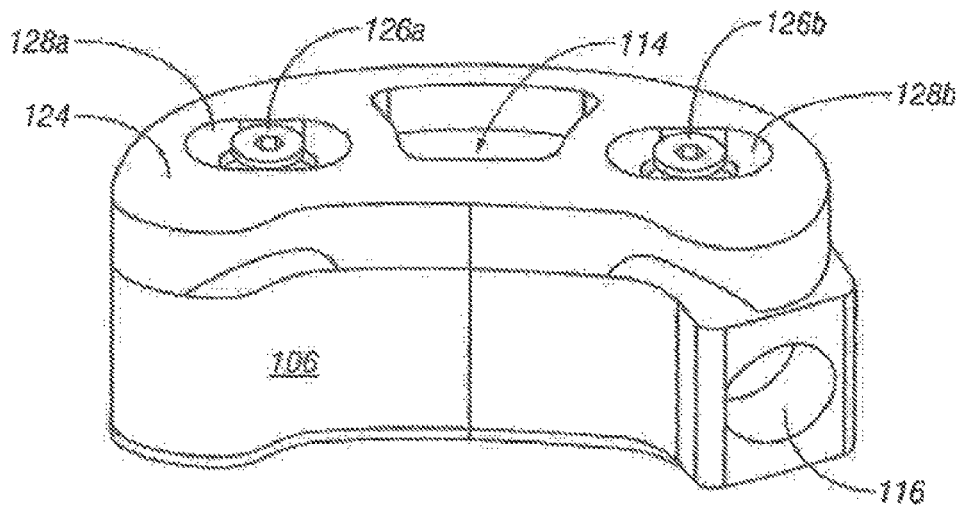
FIG. 4B is a rear perspective view of the SEC of FIG. 4A according to an aspect of the invention.

FIG. 4A shows SEC 100 from the front or anterior position with respect to the vertebral column. The SEC is shown in a closed or unexpanded position. Referring to FIGS. 4A through 4E, SEC 100 comprises a body or block 106 that defines one or more slave cylinders 108a, 108b (best seen in FIG. 5A) for corresponding pistons 110a, 110b. Pistons are provided with O-rings 112a, 112b for a tight seal with the cylinder. The pistons and cylinders cooperate to provide hydraulically extendable members disposed within the body of SEC 100 in the unexpanded state. Block 106 also defines a central cavity 114 for infusion of bone graft material into the intervertebral space when the SEC is fully expanded or during the expansion process, as will be explained.

In general, bone graft material can be any substance that facilitates bone growth and/or healing (whether naturally occurring or synthetic), such as, for example, osteoconduction (guiding the reparative growth of the natural bone), osteoinduction (encouraging undifferentiated cells to become active osteoblasts), and osteogenesis (living bone cells in the graft material contribute to bone remodeling). Osteogenesis typically only occurs with autografts.

Figure 4C:
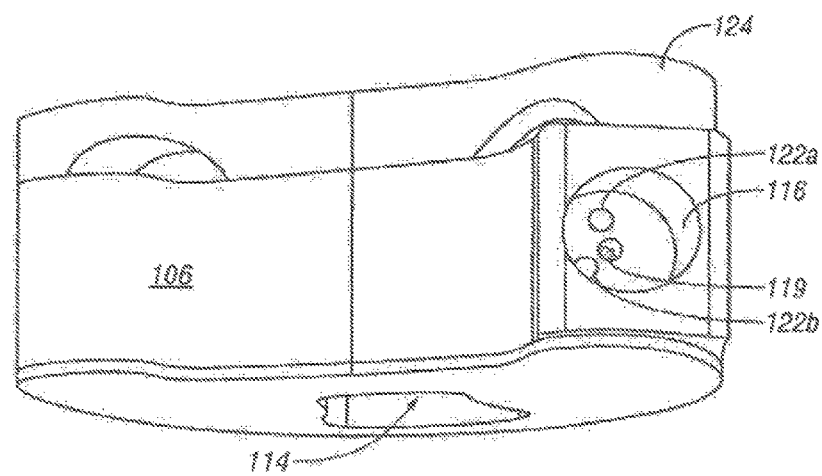
FIG. 4C is a rear perspective view of the SEC of FIG. 4A showing details of the hydraulic and bone graft input ports according to an aspect of the invention.
Figure 4D:
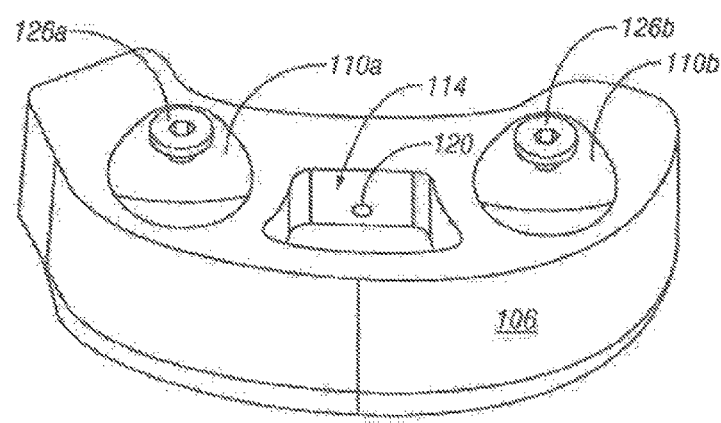
FIG. 4D is a perspective view of the SEC of FIG. 4A with the wedge plate removed for clarity.
Figure 4E:
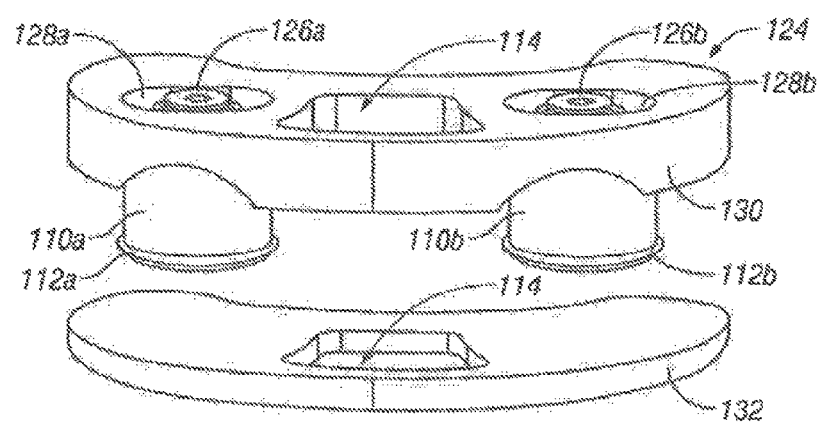
FIG. 4E is a perspective view of FIG. 4A showing the cylinders and bone graft perfusing cavity defined by the SEC body according to an aspect of the invention.
Figure 5A:
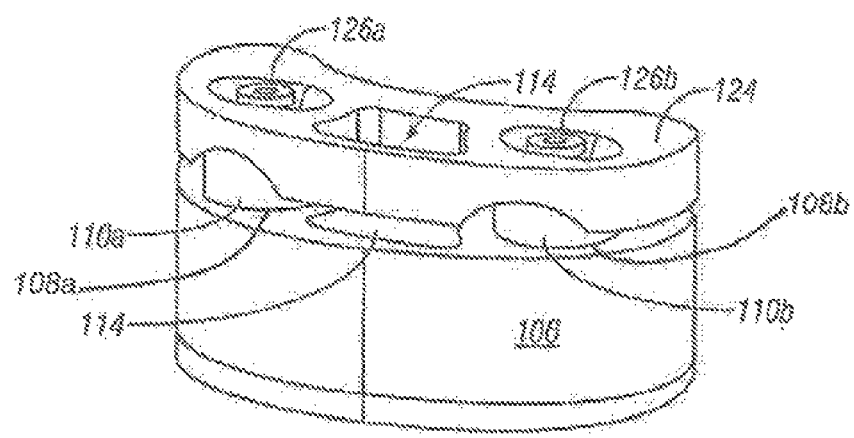
FIG. 5A is a front perspective view of the SEC in an expanded state according to an aspect of the invention.
Figure 5B:
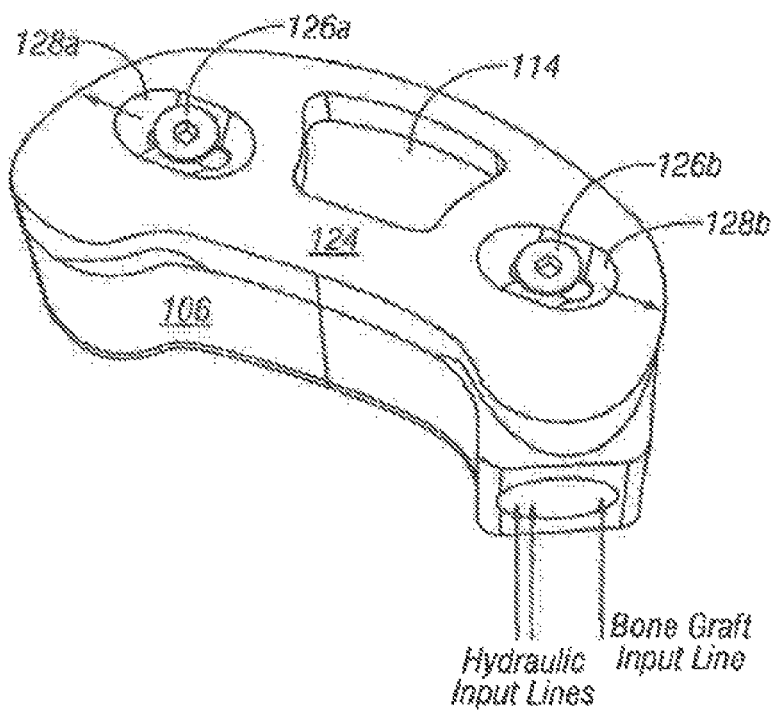
FIG. 5B is a top perspective view of the SEC showing the cavity for bone graft perfusion and recesses allowing lateral movement of the wedge according to an aspect of the invention.
Figure 5C:
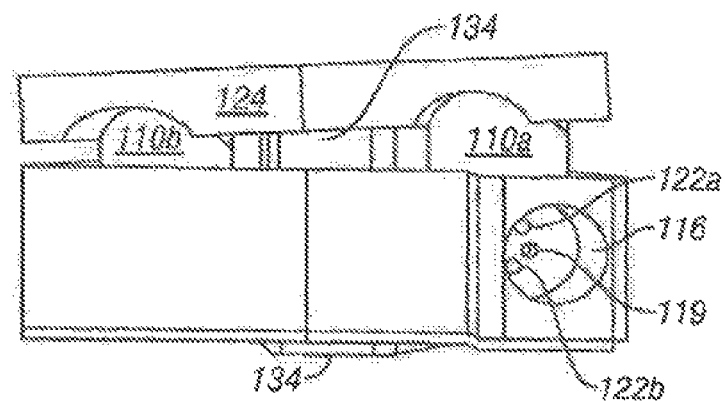
FIG. 5C is a rear perspective view of the SEC in an expanded state according to an aspect of the invention.
Figure 5D:
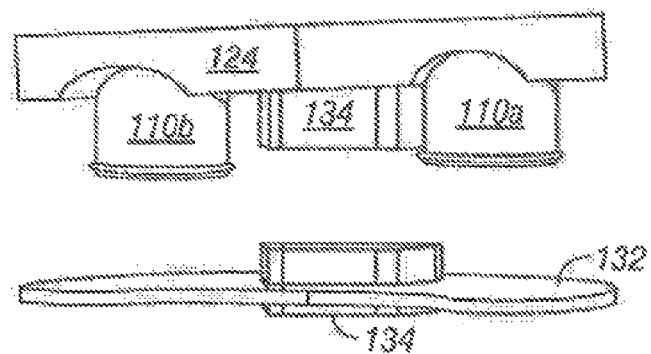
FIG. 5D is a perspective view of FIG. 5C with the SEC body removed for clarity.

As shown in FIG. 4C, block 106 further defines a central or main input port 116 for attachment of hydraulic lines and a line for transmission of a slurry or liquid bone graft material as will be explained. The block 106 defines a bone graft infusion conduit that extends from a bone graft input port 119 located in main input port 116 to a bone graft exit port 120 (see FIG. 4D) located in central cavity 114 for infusion of bone graft material therein.

Block 106 further defines local hydraulic fluid input ports 122a, 122b (FIG. 4C) that lead to corresponding slave cylinders 108a, 108b (FIG. 5A) for driving the pistons and expanding the SEC by remote control from a master cylinder located ex vivo and with greatly increased force as compared to conventional devices.

It will be appreciated that each slave piston 110a, 110b is independently controlled by a separate hydraulic line 122a, 122b connected to a master cylinder (as will be explained with reference to FIGS. 7a through 8) located away from the patient and the site of implantation, thus minimizing active intervention by surgical tools in the immediate vicinity of nerve roots. Although two slave cylinders are shown by way of example, it will be appreciated that the invention is not so limited, but on the contrary, SEC block 106 easily is modifiable to define a multiplicity of slave cylinders, each controlled independently by a separate hydraulic line, for expanding differentially to provide a substantially infinite variety of space-sensitive adjustments for unique applications.

Referring again to FIGS. 4A through 4G, an anterior/posterior corrective plate or wedge plate 124 is movably held in captured engagement on top of pistons 110a, 110b by corresponding hold down screws 126a, and 126b. Plate 124 enables spinal correction in the anterior/posterior direction as the cylinders expand vertically. Plate 124 has a bone-engaging top surface provided with two elongated slots 128a, 128b in which the hold down screws sit. The elongated slots 128a, 128b enable ease of expansion and facilitate angles between the pistons by allowing the plate 124 to move laterally slightly as pistons differentially expand. The plate also defines cavity 114 for the infusion of bone graft material, that is co-extensive with and the same as cavity 114 defined by the SEC block. This enables perfusion of the bone graft material directly through the bone engaging surface of the wedge plate into the adjacent vertebral body.

Figure 4F:
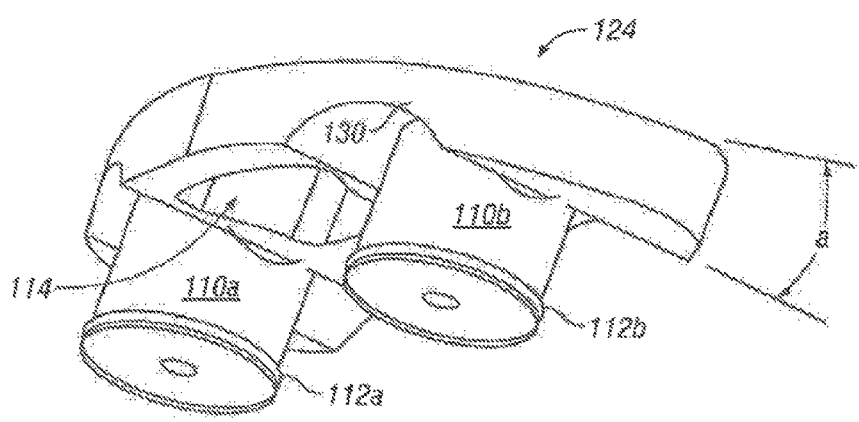
FIG. 4F shows another view of the wedge plate according to an aspect of the invention.
Figure 4G:
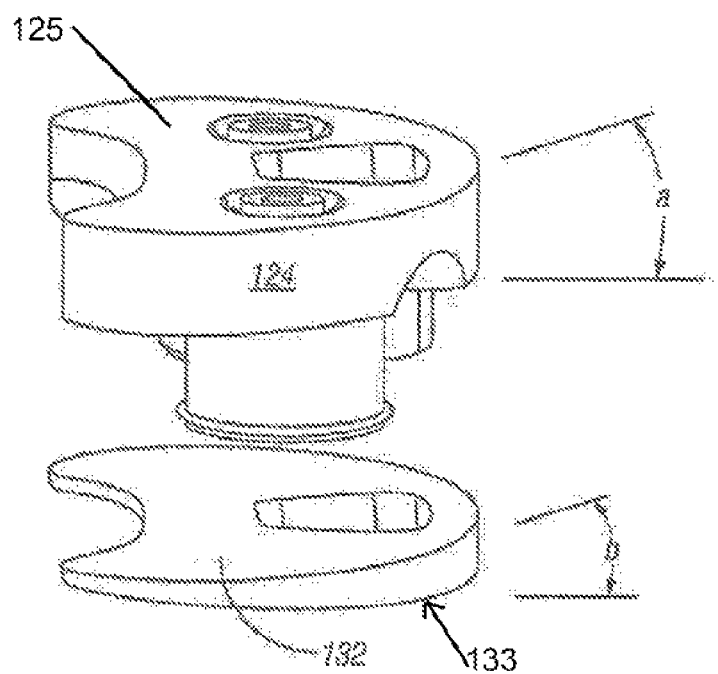
FIG. 4G shows details of the wedge plate and lordosis plate according to an aspect of the invention.

Referring to FIGS. 4F and 4G, the anterior/posterior corrective plate 124 is provided with a downwardly-extending edge 130 for engagement with the pistons as they differentially expand, to ensure that wedge plate stays firmly in place. Plate 124 provides anterior/posterior correction in that it can be angled front to back like a wedge with a correction angle a of 0-5 degrees or more. Plate 124 also defines bone graft cavity 114 for enabling bone growth conductive or inductive agents to communicate directly with the engaged vertebral endplate.

The SEC is optionally provided with a lordosis base plate 132 that includes a bone engaging surface defining a cavity co-extensive with bone graft cavity 114 for enabling perfusion of bone graft material into the adjacent engaged vertebral body. Lordosis base plate 132 also has an anterior/posterior angle b (refer to FIG. 4G) of 0-5 degrees for correcting lordosis.

Referring to FIG. 4G, top plate 124 and optional lordosis base plate 132 function as two endplates providing a corrective surface that impacts vertebral bodies for spinal correction. Top plate 124 and lordosis base plate 132 each include a bone-engaging surface 125 and 133, respectively, defining a cavity co-extensive with bone graft cavity 114 for enabling perfusion of bone graft material into the adjacent opposed vertebral body. Lordosis base plate also has anterior/posterior angle b of 0-5 degrees for correcting lordosis. Thus, the wedge plate and lordosis base plate can provide lordotic correction of 10 degrees or more.

Surgeon control over sagittal alignment is provided by differential wedge shaping of the endplates and by calculated degrees of variable piston expansion. The end plates will be constructed with 0 degrees of wedge angle anterior to posterior, or 5 degrees. Therefore, the final construct may have parallel end plates (two 0 degree endplates), 5 degrees of lordosis (one 5 degree and one 0 degree endplate), or 10 degrees of lordosis (two 5 degree implants). This implant permits unprecedented flexibility in controlling spinal alignment in the coronal and sagittal planes.

Since vertebral end plates are held together at one end by a ligament much like a clamshell, expansion of the pistons vertically against the end plates can be adjusted to create the desired anterior/posterior correction angle. Thus, the top plate 124 does not need to be configured as a wedge. Where an extreme anterior/posterior correction angle is desired, the top plate and/or base plate may be angled as a wedge with the corresponding correction angles set forth above.

FIGS. 5A through 5D show the SEC in its expanded state. Hydraulic fluid flows from a master cylinder (FIG. 7A) into the cylinders through separate hydraulic input lines that attach to hydraulic input ports 122a, 122b. Each hydraulic line is regulated independently thereby allowing a different quantity of material to fill each cylinder and piston cavity pushing the pistons and medial/lateral wedge plate upward to a desired height for effecting spinal correction.

In accordance with an aspect of the invention, the hydraulic fluid communicating the mechanical leverage from the master cylinder to the slave cylinder or syringe and pistons advantageously is a time-controlled curable polymer such as methyl methacrylate. The viscosity and curing time can be adjusted by the formulation of an appropriate added catalyst as is well known. Such catalysts are available from LOC-TITE Corp., 1001 Trout Brook Crossing, Rocky Hill, Conn. 06067. When the polymer cures, it hardens and locks the pistons and thus the desired amount of spinal correction determined by the physician is immovably in place.

It will be appreciated that the cylinder block 106 and pistons 110a, 110b, comprise a biocompatible, substantially incompressible material such as titanium, and preferably type 6-4 titanium alloy. Cylinder block 106 and pistons 110a, 110b completely confine the curable polymer that is acting as the hydraulic fluid for elevating the pistons. When the desired spinal correction is achieved by the expanded pistons, the curable polymer solidifies, locking the proper spinal alignment substantially invariantly in place. The confinement of the polymer by the titanium pistons and cylinder block provides the advantage of making the polymer and the desired amount of spinal alignment substantially impervious to shear and compressive forces.

For example, even if it were possible to compress the polymer it could only be compressed to the structural limit of the confining cylinder block. That is, by placing the curable polymer into the 6-4 titanium cylinder block wherein two or more cylinders are expanded, the polymer becomes essentially non-compressible especially in a lateral direction. It will be appreciated that 6-4 titanium cylinder block confining the hydraulic material provides extreme stability and resistance to lateral forces as compared to a conventional expanding implant. Further, there is no deterioration of the curable polymer over time in term of its structural integrity because it is confined in the titanium alloy body.

The use of the present 6-4 titanium cylinder block configuration can withstand compressive forces in excess of 12,000 Newtons or approximately 3000 pounds of compressive force on the vertebrae. This is not possible in a conventional expanding structure wherein the expanding polymer is not confined by an essentially incompressible titanium body.

In accordance with another aspect of the invention, injectable bone graft material 134 is provided along a separate bone graft input line to bone graft input port 119 for infusion into cavity 114 through bone graft exit port 120.

The bone graft input line is controlled at the master cylinder or from a separate source to enable a pressure-induced infusion of bone graft material 134 through cavity of the bone engaging surfaces of the SEC into adjacent vertebral bone. Thus, the bone graft material fills, under pressure, the post-expansion space between adjacent vertebral bodies. This achieves substantially complete perfusion of osteo-inductive and/or osteo-conductive bone graft material in the post expansion space between the vertebral bodies resulting in enhanced fusion (refer to FIGS. 5C, 5D).

Figure 6:
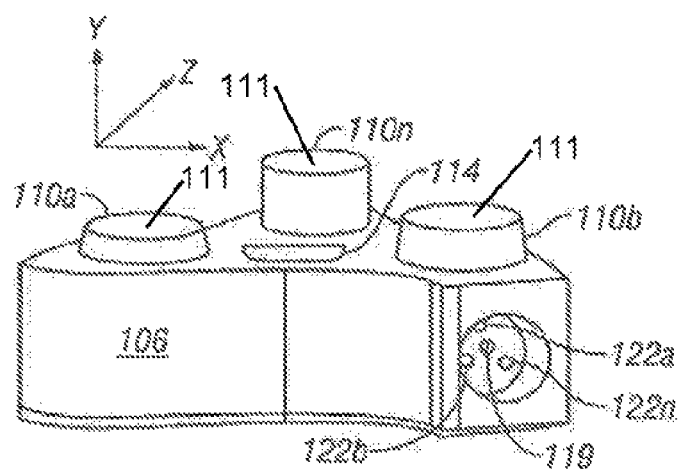
FIG. 6 is a perspective view of an alternative embodiment of the SEC according to an aspect of the invention.

Referring to FIG. 6, an alternate embodiment of the SEC comprises multiple slave cylinders and corresponding pistons 110a, 110b, 110n are provided in SEC body 106. Each of the multiple slave cylinders and pistons 110a, 110b, 110n is provided with a separate, associated hydraulic line 122a, 122b, 122n that communicates independently with a corresponding one of a plurality of cylinders in the master cylinder for independently controlled expansion of the slave cylinders at multiple elevations in three dimensions (X, Y and Z axes).

At the master cylinder, multiple threaded cylinders (or disposable syringes) and pistons are provided, each communicating independently through a separate hydraulic line 122a, 122b, 122n with a corresponding one of the slave cylinders and pistons 110a, 110b, 110n in the SEC.

The bone engaging surfaces of the multiple pistons 110a, 110b, 110n provide the corrective surface of the SEC. Thus, by appropriate adjustment of the pistons in the master cylinder, or depending on fluid installed via separate syringes, the surgeon can independently control expansion of the slave pistons in the SEC to achieve multiple elevations in three dimensions for specialized corrective applications. A top or wedge plate is not necessary.

The bone engaging surface 111 of the slave pistons 110a, 110b, 110n in the SEC may be provided with a specialized coating for bone ingrowth such as hydroxyapetite. Alternatively, the bone-engaging surface 111 of the SEC pistons may be corrugated, or otherwise provided with a series of bone engaging projections or cavities to enhance fusion.

As previously explained, the hydraulic fluid communicating the mechanical leverage from the master cylinder to the SEC slave cylinders and pistons 110a, 110b, 110n is a time-controlled curable polymer such as methyl methacrylate that locks the SEC immovably in place after curing, at the desired three dimensional expansion.

As set forth above, injectable bone graft material is provided along a separate bone graft input line to bone graft input port 119 for infusion into cavity 114 and into the inter body space between the SEC and adjacent bone.

The surgeon by adjustment of the master cylinder is able to provide remotely a controlled angle of the SEC corrective surface to the medial/lateral (X axis) and in the anterior, posterior direction (Z axis). The surgeon also can adjust the SEC in the vertical plane moving superiorly/inferiorly (Y axis) from the master cylinder or power/flow source to control implant height. Thus, three-dimensional control is achieved remotely through a hydraulic line with minimal trauma to a patient. This aspect of the invention advantageously obviates the need to manually manipulate the SEC implant at the site of intervention to achieve desired angles of expansion. Such conventional manual manipulation with surgical tools into the intervention site can require further distracting of nerve roots and cause potential serious trauma to a patient.

Figure 7A:
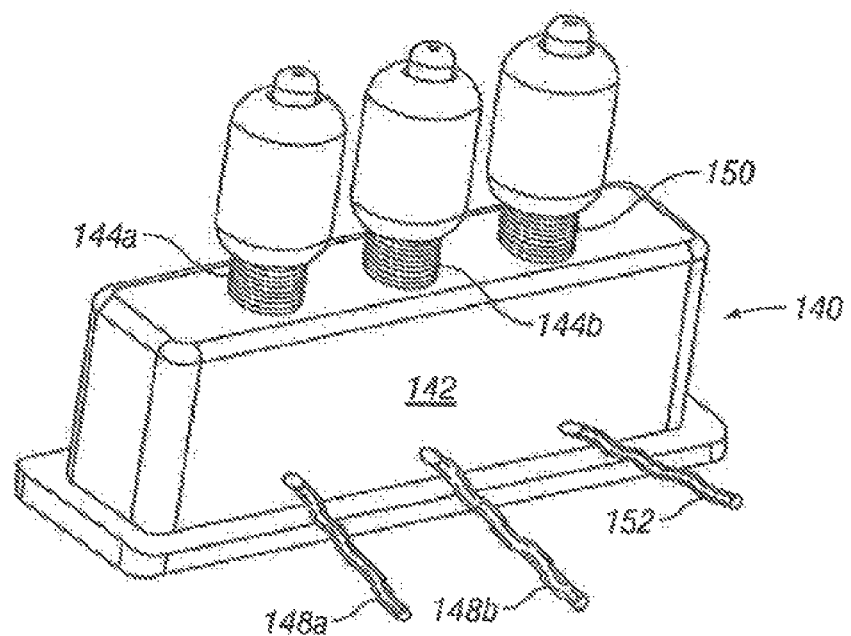
FIG. 7A is a perspective view of a master cylinder for hydraulic control of the SEC according to an aspect of the invention. A variety of alternative embodiments are available, most simply disposable syringes used for piston expansion.
Figure 7B:
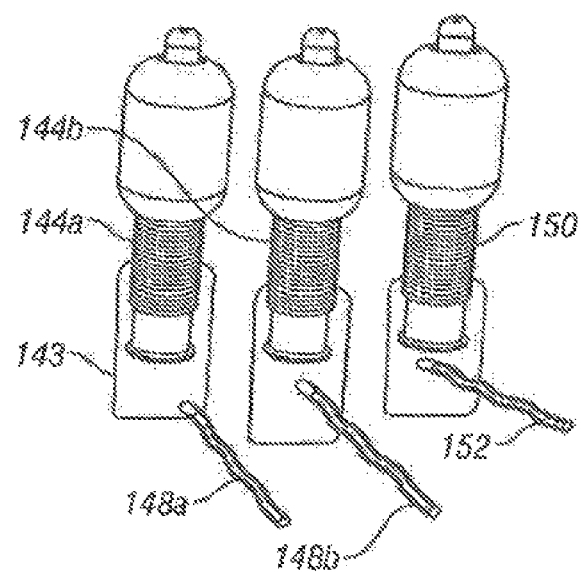
FIG. 7B is a view of the interior of FIG. 7A.

Referring to FIGS. 7A and 7B, in accordance with an aspect of the invention, a master cylinder 140 located remotely from the patient, provides controlled manipulation and adjustment of the SEC in three dimensions through independent hydraulic control of slave cylinders 110a, 110b in the SEC. Master cylinder 140 comprises a cylinder block 142, defining two or more threaded cylinders 143. Corresponding screw down threaded pistons are rotated downward into the threaded cylinders thereby applying force to a hydraulic fluid in corresponding hydraulic control lines that communicate independently with and activate corresponding slave cylinders 110a, 110b in the SEC with mechanical leverage. The rotational force for applying the mechanical leverage at the slave cylinders is controlled by thread pitch of the threaded pistons in the master cylinder, or in an alternate embodiment controlled by use of syringes, one acting as a master cylinder for each piston or slave cylinder to modulate piston elevation.

In FIG. 7B threaded pistons 144a, 144b are provided in hydraulic cylinders communicating through hydraulic lines 148a, 148b that are coupled to hydraulic input ports 116a, 116b for independent hydraulic control of slave cylinders 110a, 110b as previously explained.

Another threaded cylinder and piston assembly 150 is supplied with a quantity of bone graft material in slurry or liquid form and operates in the same way to provide the bone graft material under pressure to the SEC bone graft input port 119 through bone graft supply line 152. Thus, bone graft material is forced under pressure from the master cylinder through cavity 114 and into the intervertebral space.

Figure 8:
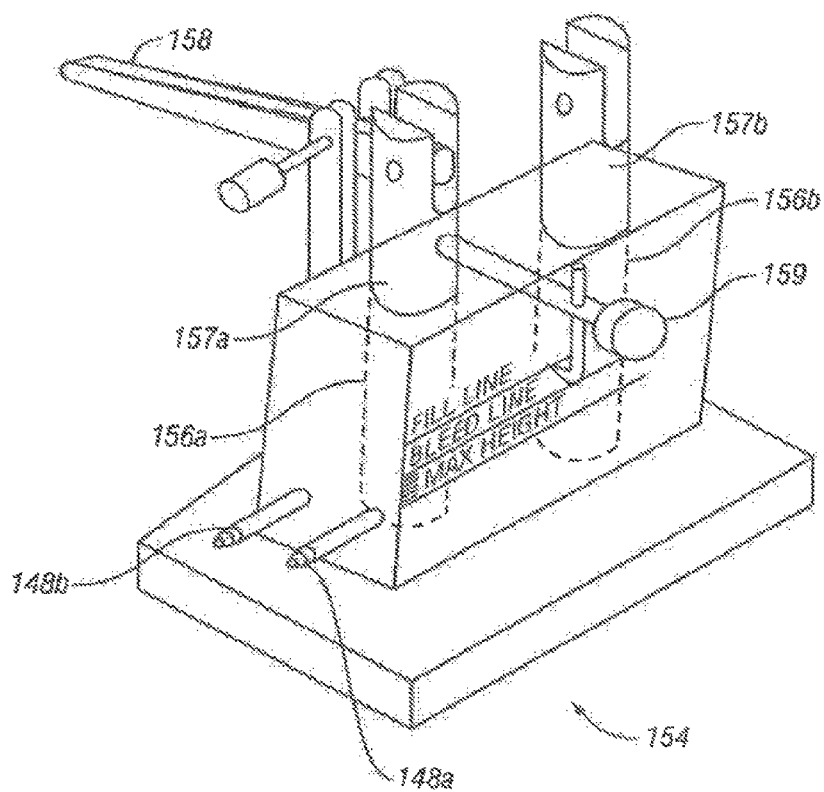
FIG. 8 is a perspective view of an alternate embodiment of the master cylinder according to an aspect of the invention.

Referring to FIG. 8, an alternate embodiment of a master cylinder is provided for individual hydraulic control of each slave piston in the SEC implant. A master cylinder 154 is provided with two or more cylinders 156a, 156b, and associated pistons 157a, 157b. A lever 158 controlled by the surgeon is attached to each piston. Hydraulic fluid feeds through lines 148a 148b into the inserted SEC implant. The lever creates a ratio of 1 pound to 10 pounds of pressure inside the slave cylinders in the SEC and thus against vertebral end plates. Mechanically this provides a 10:1 advantage in lift force for the surgeon. The surgeon's required force application is multiplied via the lever and hydraulic system to create a controlled expansion of the SEC against the end plates as previously described to create any desired spine vertebral correctional effect in three dimensions.

If the surgeon uses one pound of force on the lever, the piston exerts 10 pounds of force. The piston in the master cylinder displaces the hydraulic fluid through hydraulic lines 148a, 148b. The hydraulic lines are flexible conduit no more than 3 mm in diameter. Thin hydraulic lines are desirable to increase mechanical advantage at the slave cylinders in the SEC. If one pound of pressure is exerted on the handle, the corresponding piston in the SEC would have 10 pounds of lifting force. If each slave piston inside the SEC implant has 200 pounds of lifting force, the required amount of pressure applied by the surgeon to the master piston cylinder is 20 pounds, or one tenth the amount, consistent with the predetermined mechanical advantage.

In usual cases, where the surgeon has a patient in a partially distracted anatomic, anesthetized and relaxed position under anesthesia, 30 pounds of force may be required for implant expansion upon the vertebral bone endplates. The surgeon in that case would need to apply only 3 pounds of pressure to lever 158. Different ratios may be introduced to optimize distraction force while minimizing injection pressures.

The pressure application process is guided by normal surgical principles, by visual checkpoints, and by a safety gauge that illustrates the amount of expansion that has been exerted in direct correlation with the implant expansion process. The gauge indicates the height of the slave pistons and thus the vertical and angular expansion of the SEC. This translates to an ability to clarify the percentage of lateral expansion. That is, if the surgeon chooses to create an angle, he expands the right slave cylinder, for example, 14 mm and left slave cylinder 12 mm.

The master cylinder 154 preferably comprises transparent plastic to enable visual indication of the height of the hydraulic fluid therein, or a translucent plastic syringe to facilitate exact measured infusion of the slave cylinder implant expanding pistons. A knob 159 for setting gauge height is provided in each cylinder. An indicator attached to the knob registers the cylinder height with respect to a fill line, bleed line or maximum height line. The master cylinder and slave cylinders are filled with hydraulic fluid. Air is removed by bleeding the cylinders in a well-known manner. The knob indicator is registered to the bleed line. A series of incremental marks are provided between the bleed line and the maximum height line to show the surgeon the exact height of the slave cylinder in response to the surgeon's control inputs to the master cylinder.

It will be appreciated that the master and slave hydraulic system interaction can have many equivalent variations. For example, the master cylinder function of master cylinder 154 also can be provided by one or more syringes. Each syringe acts as a master cylinder and is coupled independently with a corresponding slave cylinder through a thin hydraulic line for independent activation as previously described. A single syringe acting as a master cylinder also may be selectively coupled with one or more slave cylinders for independent activation of the slave cylinders. As is well known, series of gradations are provided along the length of the syringe that are calibrated to enable the surgeon to effect a precise elevation of a selected piston at the corresponding slave cylinder in the implant.

As previously explained, the SEC implant also expands vertically the intervertebral space from 10 mm to 16 mm or more. Additionally, by changing the diameter of the piston inside the master cylinder, the force exerted into the slave cylinder could be multiplied many fold so as to create major force differentials. The foregoing features provide the surgeon with an ability to establish a spinal correction system that is a function of the needed change to correct a deformity, so as to produce normal alignment.

Figure 9A:
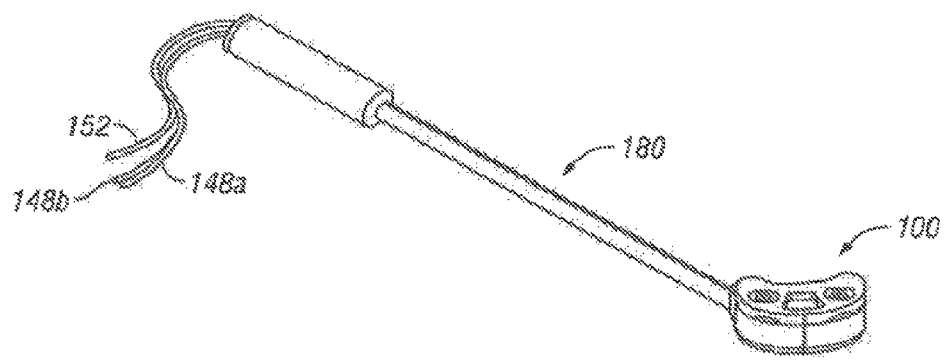
FIG. 9A is a perspective view of the insertion tool holding the SEC, hydraulic lines and bone graft supply line according to an aspect of the invention.
Figure 9B:
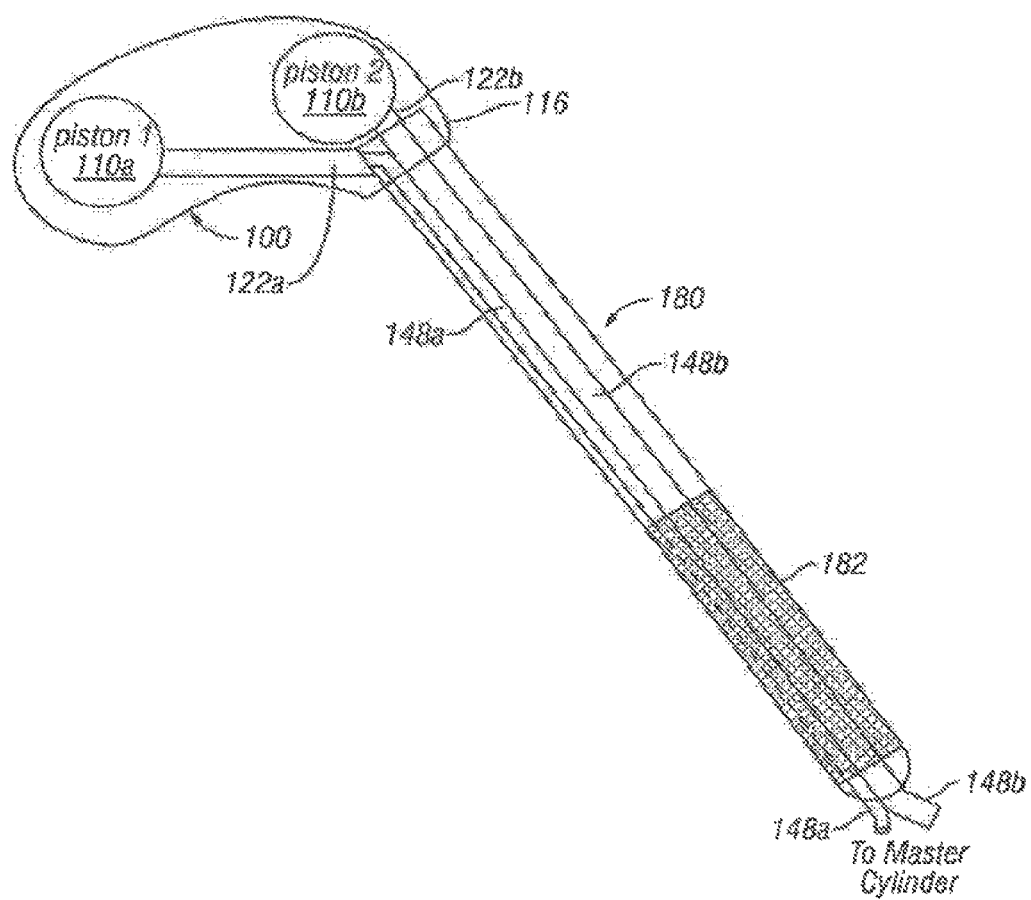
FIG. 9B is a close-up view of the insertion tool of FIG. 9A.

Referring to FIG. 9A, it will be appreciated that hydraulic control lines 148a and 148b and bone graft supply line 152 are characterized by a minimal size and are provided in the interior of a very narrow insertion tool 180 (FIGS. 9A and 9B). The insertion tool 180 is small enough to insert the SEC 100 posteriorly into the narrow insertion opening without risk of serious trauma to the patient. An enlarged view of the insertion tool 180 (simplified for clarity) is shown in FIG. 9B. The insertion tool 180 includes a handle 182 and hollow interior for housing hydraulic control lines and a bone graft supply line (not shown for clarity). The hydraulic control lines and bone graft supply line connect through a proximal end of the insertion tool to the master cylinder. A distal or insertion end of the tool holds the SEC 100. In a preferred mode, the insertion end of the insertion tool conformably fits in the SEC hydraulic input port 116. Hydraulic control lines and the bone graft supply line are connected to the hydraulic input ports 122a, 122b and bone graft supply input port respectively, prior to surgery.

The bone graft supply and hydraulic control lines are safely retracted after the SEC is positioned. The hydraulic lines can be released by cutting after the operation since the hydraulic fluid hardens in place.

When the SEC is locked in position by the surgeon, the insertion tool and hydraulic tubes are removed and the curable polymer remains in the SEC slave cylinders.

In accordance with an aspect of the invention, the hydraulic fluid controlling the movement of the SEC is a time-controlled curable polymer that hardens after a pre-determined time period, locking the SEC insert immovably in a desired expanded position. The hydraulic fluid is preferably methylmethacrylate or other similar inexpensive polymer, with a time-controlled curing rate. Time-controlled curable polymers typically comprise a catalyst and a polymer. The catalyst can be formulated in a well-known manner to determine the time at which the polymer solidifies. Such time-controlled curable polymers are commercially available from several manufacturers such as LOCTITE Corp., Henkel-Loctite, 1001 Trout Brook Crossing, Rocky Hill, Conn. 06067.

As is well understood by one skilled in the art, any equivalent curable polymer that has a first flowable state for conveying hydraulic force, and that transitions to a second solid state upon curing may be employed. In the first state, the curable polymer transfers the application of force hydraulically from the master cylinder to the slave cylinders, such that corrective action is achieved by elevating the slave pistons. The curable polymer transitions to a second solid state upon curing such that the corrective elevation of the slave pistons is locked in place. Such an equivalent curable polymer is a polymer that is cured through the application of either visible or ultraviolet light or other radiation source which activates the polymer to transition to a solid state. Another methyl methacrylate liquid polymer when combined with powder becomes a viscous fluid as soon as the powder and liquid are blended; it is initially thin and free flowing. Gradually, in minutes, it begins to thicken, transforming state through paste and puddy to cement-like solid once inside the pistons, thus fixing the SEC at a precise correction amount in its expanded position.

An example of such a light curable polymer is UV10LC-12 made by MASTER BOND Inc., of Hackensack, N.J. Such polymers are characterized by a fast cure time upon exposure to a visible or a UV light source. Depending upon the intensity of the light source, cure times range from a few seconds to less than a minute. As is well understood by one skilled in the art, an extremely thin fiber optic line may be incorporated as an additional line along with the multiple hydraulic lines shown in FIGS. 10A and 10B for conveying light from a light source directly to the polymer in the slave cylinders to effect curing.

Alternatively, a curable polymer may be activated by a radiation source such as low level electron beam radiation to cure or initiate curing. An electron beam advantageously can penetrate through material that is opaque to UV light and can be applied directly to lock the pistons in their elevated or corrective position.

It will be appreciated that the amount of applied stress required to cause failure of the corrective implant is substantial due to the confinement of the cured polymer completely within the body of the implant, that is, the cylinder block that is comprised of 6-4 titanium. This is particularly advantageous since the confinement within the titanium body enables the corrective position of the implant to withstand compressive forces up to the structural failure limit of the titanium body; that is, to withstand compressive forces in a range of from 8000 up to 12,000 Newtons.

Figure 10A:
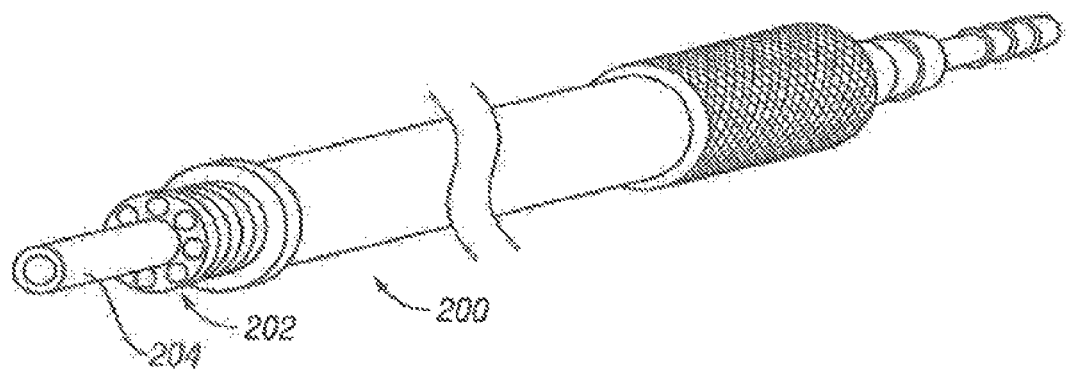
FIG. 10A shows one embodiment of a hydraulic line for independent control of multiple slave cylinders according to an aspect of the invention.
Figure 10B:
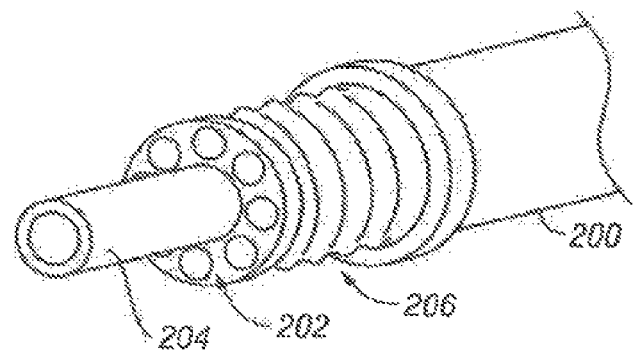
FIG. 10B shows a close up of the fitting for the hydraulic line of FIG. 10A according to an aspect of the invention.

Referring to FIGS. 10A and 10B, a hydraulic line 200 is provided for remote hydraulic control of a plurality of slave cylinders of the SEC from a master cylinder. Hydraulic line 200 comprises a plurality of individual hydraulic lines 202 disposed about a central axis. Each hydraulic line 202 provides independent activation of a separate slave cylinder from a master cylinder as previously explained. A bone graft supply line 204 is provided along the central axis of line 200. Individual hydraulic lines 202 can be aligned and connected with corresponding slave cylinder input ports prior to insertion of the SEC for providing independent hydraulic control to each of the slave cylinders. A threaded end 206 can be inserted into a similarly threaded central input port 116 of the SEC to prevent pull out.

In a further alternative embodiment of the present invention, as illustrated for example in FIGS. 11-15, SEC 300 includes a block or body 306 defining cylinders 308 for receiving pistons cooperating with a top plate 324 substantially as previously described. The body 306 of SEC 300 also defines a central cavity 314 to receive bone graft material for communication with the intervertebral space when implanted. Top plate 324 also provides a central opening aligned with central cavity 314 to facilitate such communication. As shown, for example in FIG. 11, top plate 324 may be provided with a textured bone engagement surface 311 on the superior surface thereof and the central opening may be shaped to match the shape of central cavity 314. The textured surface is configured to provide for greater security and fixation between the vertebral body and SEC 300, and is not limited to the pattern shown, but may be of any appropriate configuration for enhancing fixation as will be appreciated by persons of ordinary skill in the art.

Figure 11:
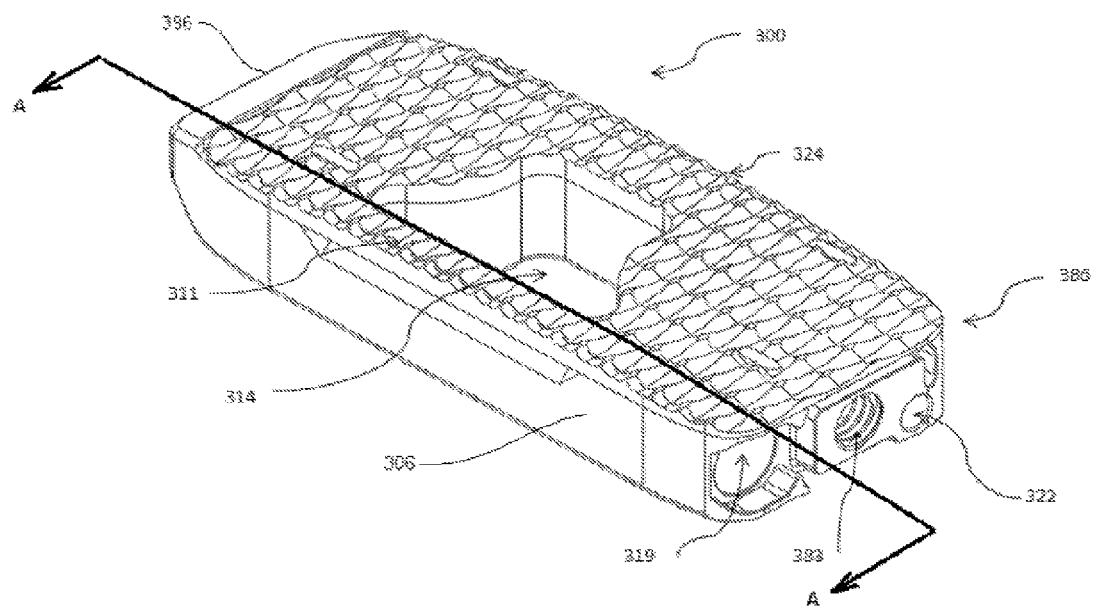
FIG. 11 is a perspective view of a further alternative embodiment of an SEC according to another aspect of the invention.

In this exemplary embodiment, SEC 300 includes a graft infusion port 319 in communication with the central graft cavity 314, which may be positioned laterally on a proximal face 386 of body 306 as shown in FIG. 11. Graft infusion port 319 may be located laterally of an attachment port 383, which is where the insertion tool 380 is connected to the SEC 300 via a threaded connector and rotary actuator 406 (see FIG. 14). Hydraulic line port 322, communicating with passages leading to cylinders 308, may be located laterally opposite attachment port 383 on proximal face 386 to receive hydraulic supply line 402 for actuation of the pistons. Distal face 396, opposite the attachment port, may present narrowed leading edge to facilitate insertion and placement of SEC 300 between adjacent vertebral bodies.

Figure 13:
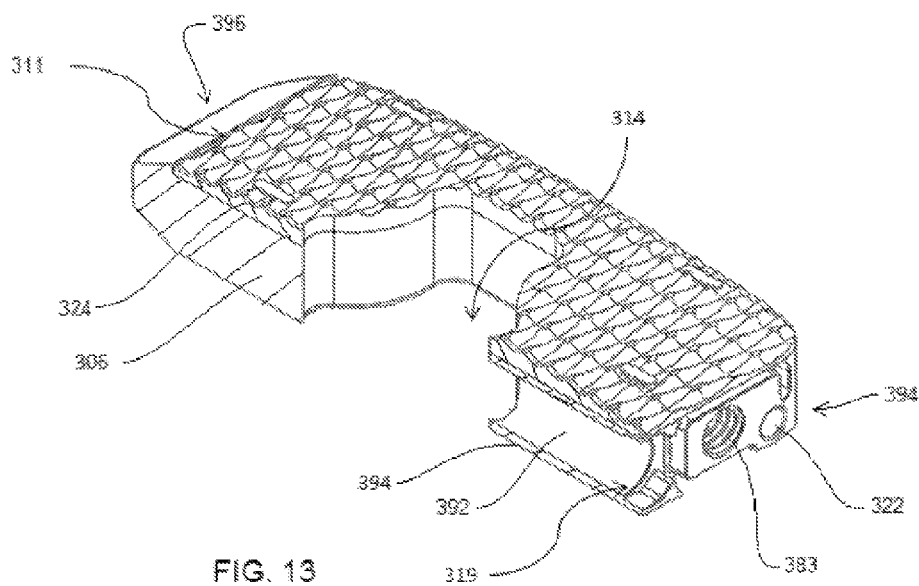
FIG. 13 shows a cross-section through line A-A in FIG. 11.
Figure 12:
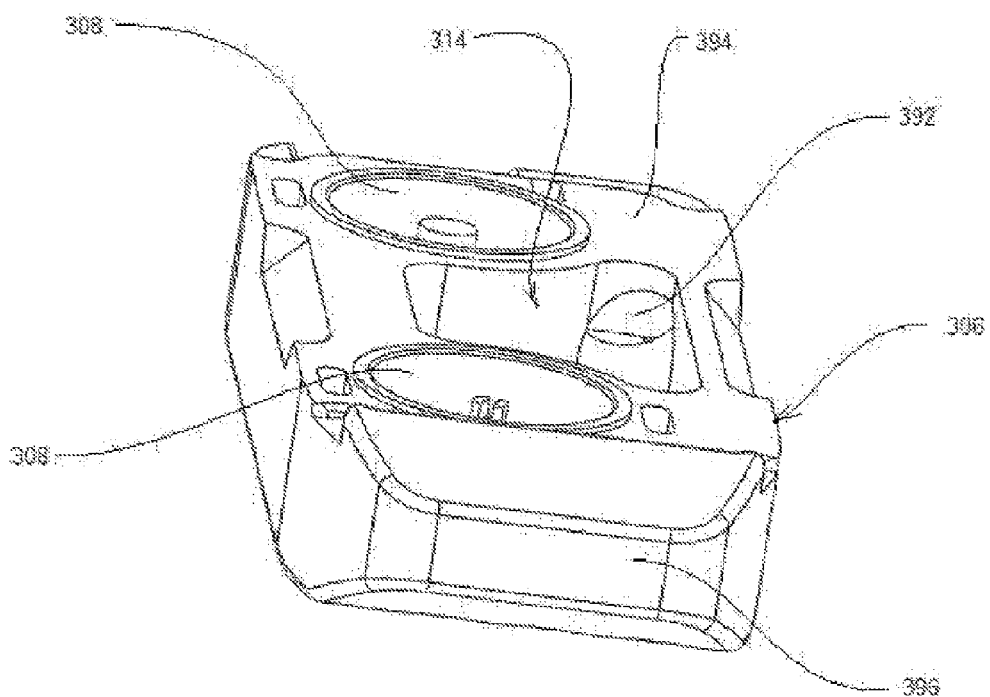
FIG. 12 is a perspective distal view of the exemplary embodiment shown in FIG. 11, with the top plate and pistons removed.

As shown, for example, in FIGS. 12 and 13, the graft infusion port 319 communicates with the central cavity 314 through passage 392, which traverses the proximal wall 394 of block 306. Graft slurry or other bone growth promoting material infused through the graft port 319 flows directly into the central cavity 314 from passage 392. The relatively large diameter of port 319 and passage 392 allow for unobstructed flow of material into the central cavity. Depending on the size of the implant and the amount of height to be achieved through extension of the pistons, this can be particularly valuable because the central cavity 314 enlarges as the SEC 300 expands. A free flow of bone graft material with sufficient volume is required to fill the enlarged volume of central cavity 314 after expansion. For example, in an implant with a width of about 18 mm, a length of about 50 mm, and a height of about 8 mm, which is expanded after placement to a height of about 12 mm, passage 392 may have an internal diameter of about 6 mm. In general, to provide an unobstructed flow of bone graft material, particularly in slurry form, passage 392 (and port 319) may be sized such that the ratio of the diameter of passage to the unexpanded implant height would be in the range of about 55-80% or more specifically about 60-75%.

Figure 14:
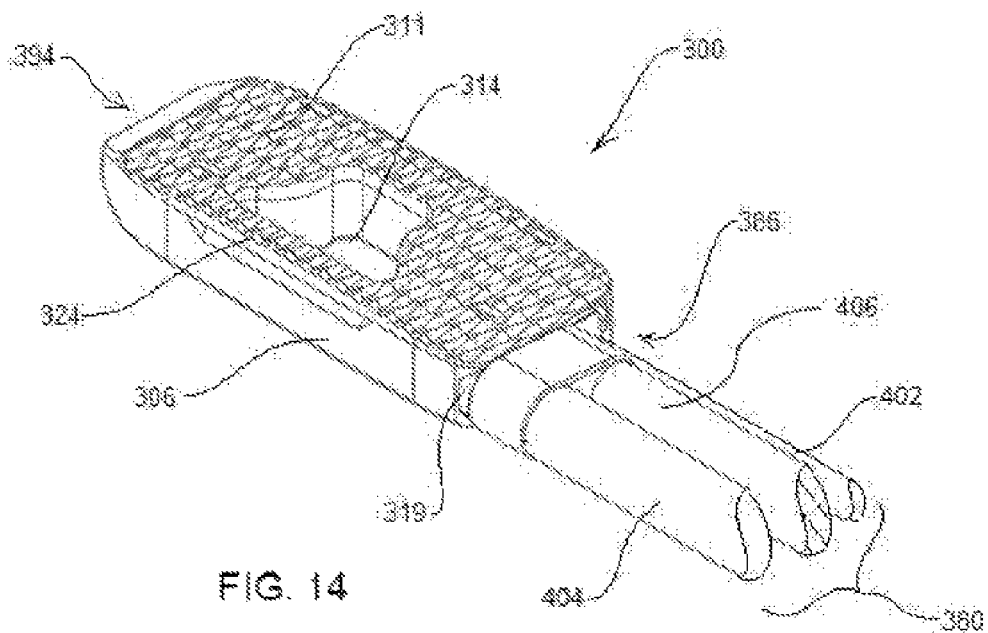
FIG. 14 is a perspective view of the exemplary embodiment shown in FIG. 11 with an attached insertion tool.
Figure 15:
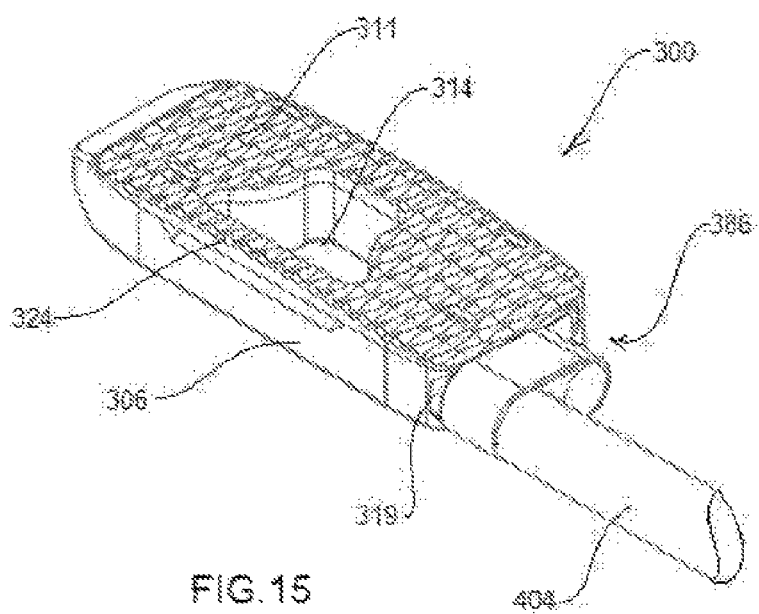
FIG. 15 is a perspective view of the exemplary embodiment shown in FIG. 11 with an attached bone graft material supply line.

As previously mentioned, with the graft infusion port 319 located lateral of the attachment port 383, the bone graft supply line 404 of insertion tool 380 can also be located lateral to the hydraulic lines 402 as shown in FIG. 14. However, this parallel, lateral arrangement may make insertion tool 380 wider, possibly creating difficulty in passing sensitive neural structures in some anatomies. Where the lateral width of the insertion tool is of concern, such concern may be addressed by providing the bone graft supply line 404 separate from an insertion tool including only the rotary actuator 406 and hydraulic supply line 402, such that bone graft supply line 404 may be placed separately and only after the SEC 300 is implanted and expanded, and the insertion tool removed, as shown in FIG. 15. In this case, a collar may be provided that also attaches in attachment port 319 to provide additional security for the bone graft supply line attachment.

In summary, remote hydraulic control of a spinal implant is particularly advantageous in a posterior insertion procedure because there is no anatomic room for mechanical linkage or tooling in the proximity of the adjacent spinal cord and neurovascular complex. The hydraulic control provided by the present invention provides significant mechanical leverage and thus increased force to an extent that has not previously been possible. Further, such hydraulic force is selective in both direction and magnitude of its application.

It is now possible to expand fenestrated endplates to support the anterior spinal column. This will create immediate and reliable firm fixation that will lead to immediate stabilization of the functional spinal motion segment, and immediate correction of complex interbody deformities in the sagittal and coronal plane.

The SEC provides advantages over currently existing technology that include correction of coronal plane deformity; introduction of interbody lordosis and early stabilization of the interbody space with rigidity that is greater than present spacer devices. This early stability may improve post-operative pain, preclude the need for posterior implants including pedicle screws, and improve the rate of successful arthrodesis. Importantly, the SEC provides improvement of space available for the neural elements while improving lordosis. Traditional implants are limited to spacer effects, as passive fillers of the intervertebral disc locations awaiting eventual fusion if and when bone graft in and around the implant fuses. By expanding and morphing into the calculated shape which physiologically corrects spine angulation, the SEC immediately fixes the spine in its proper, painless, functional position. As infused osteoinductive/osteoconductive bone graft materials heal, the patient becomes well and the implant becomes inert and quiescent, embedded in bone, and no longer needed.

While the invention has been described in connection with what are presently considered to be the most practical and preferred embodiments, it is to be understood that the invention is not limited to the disclosed exemplary embodiments and alternatives as set forth above, but on the contrary is intended to cover various modifications and equivalent arrangements included within the scope of the following claims.

For example, equivalent expansion surfaces can be provided for stabilizing the expanding SEC against the bone. Other compositions of additives may be used for the hydraulic fluid that achieves remote controlled expansion of the SEC in three dimensions. Similarly, various types of biogenic fluid material for enhancing bone growth may be injected through one or more lines to the SEC and different exit apertures may be provided to apply bone graft material to fill the intervertebral space, without departing from the scope of the invention.

The implant itself can be made of, for example, such materials as titanium, 64 titanium, or an alloy thereof, 316 or 321 stainless steel, biodegradeable and biologically active materials, e.g. stem cells, and polymers, such as semicrystalline, high purity polymers comprised of repeating monomers of two ether groups and a key tone group, e.g. polyaryetheretherketone (PEEK) TM, or teflon.

Finally, the implant may provide two or more pistons that are operated concurrently to provide coordinated medial/lateral adjustment of a patient's spine for scoliosis, with anterior/posterior adjustment of the patient's spine to create natural lordosis, with relative anterior expansion greater than posterior expansion.

Therefore, persons of ordinary skill in this field are to understand that all such equivalent processes, arrangements and modifications are to be included within the scope of the following claims.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A surgical method comprising:
    providing an interbody implant having first and second bone contacting surfaces, the interbody implant including a port having a first interlocking structure;
    inserting the interbody implant between first and second vertebral bodies using an insertion tool having a second interlocking structure detachably interlocked with the first interlocking structure of the port, such that the first bone contacting surface contacts the first vertebral body and the second bone contacting surface contacts the second vertebral body;
    moving the first and second bone contacting surfaces away from one another after the inserting step; and
    subsequent to the moving step, supplying bone graft material into the interbody implant through the port such that the bone graft material moves from a first location outside of the interbody implant to a second location inside the interbody implant through the port, in order to facilitate infusion of the bone graft material into an intervertebral space.

2. The surgical method of claim 1, wherein the interbody implant has an extendable member and the moving step comprises extending the extendable member by supplying fluid to the extendable member.

3. The surgical method of claim 2, wherein the extendable member comprises a piston within a cylinder and the moving step comprises supplying fluid to the cylinder.

4. The surgical method of claim 1, wherein the interbody implant has a plurality of extendable members coupled to the first and second bone contacting surfaces and the moving step comprises extending the plurality of extendable members to move the first and second vertebral contacting surfaces away from one another.

5. The surgical method of claim 4, wherein the moving step comprises extending each of the plurality of extendable members independently of one another.

6. The surgical method of claim 1, wherein the first bone contacting surface is disposed on a base member and the second bone contacting surface is disposed on a pressure applying member and the moving step comprises moving the pressure applying member away from the base member.

7. The surgical method of claim 1, wherein the interbody implant includes a bone graft window when the first and second bone contacting surfaces are moved away from one another, and wherein the method further includes transferring the bone graft material through the bone graft window into an intervertebral space.

8. The surgical method of claim 1, wherein the interbody implant includes a locking system and the method further comprises locking the interbody implant in an expanded state as the first and second bone contacting surfaces are moved away from one another.

9. The method of claim 8, wherein the locking step further comprises automatically locking the interbody implant in the expanded state as the first and second bone contacting surfaces are moved away from one another.

10. The surgical method of claim 1, further comprising providing bone graft material to the interbody implant prior to the inserting step.

11. The surgical method of claim 1, wherein the supplying step comprises supplying the bone graft material into the interbody implant via the insertion tool.

12. A method for fusing first and second vertebral bodies comprising:
    implanting an interbody implant between the first and second vertebral bodies using an insertion tool having a second interlocking structure detachably interlocked with a first interlocking structure of a connector on the interbody implant, so that a first member contacts the first vertebral body and a second member contacts the second vertebral body, the interbody implant having a distal portion and a proximal portion;
    expanding the first and second members away from each other to increase the size of a cavity formed in the implant after the implanting step; and
    supplying a bone graft material into the increased size cavity of the interbody implant through an aperture in the implant such that the bone graft material moves from a first location outside of the interbody implant to a second location inside the interbody implant through the aperture, wherein the aperture and the connector are both disposed on the proximal portion of the interbody implant.

13. The surgical method of claim 12, wherein the interbody implant has an extendable member adapted to be extended by fluid and the moving step comprises extending the extendable member via fluid.

14. The surgical method of claim 13, wherein the fluid is a curable polymer.

15. The surgical method of claim 13, wherein the interbody implant comprises a body to house at least a portion of the extendable member and wherein expanding the first and second members away from each other includes expanding at least one of the first and second members away from the body.

16. The surgical method of claim 13, wherein the extendable member comprises a piston within a cylinder and the moving step comprises supplying hydraulic fluid to the cylinder to expand the piston away from the cylinder.

17. The surgical method of claim 12, wherein the interbody implant has a plurality of extendable members coupled to the first and second members and the moving step comprises extending at least one of the plurality of extendable members to move the first and second members away from one another.

18. The surgical method of claim 17, wherein the moving step comprises extending each of the plurality of extendable members independently of one another.

19. The surgical method of claim 12, further comprising providing bone graft material to the interbody implant prior to the inserting step.

20. The surgical method of claim 12, wherein the cavity extends completely through the interbody implant along an axis transverse to the first and second members.

21. The surgical method of claim 12, wherein the interbody implant includes a locking system and the method further comprises locking the interbody implant in an expanded state as the first and second members are moved away from one another.

22. The surgical method of claim 12, wherein the supplying step comprises supplying the bone graft material into the increased size cavity of the interbody implant via the insertion tool.

\* \* \* \* \*